United States Patent
Yamada

(10) Patent No.: US 12,366,441 B2
(45) Date of Patent: Jul. 22, 2025

(54) DETECTOR OR PHOTOMULTIPLIER TUBE (PMT) GAIN CONTROL OVER TIME

(71) Applicant: Canon U.S.A., Inc., Melville, NY (US)

(72) Inventor: Daisuke Yamada, Cambridge, MA (US)

(73) Assignee: Canon U.S.A., Inc., Melville, NY (US)

(*) Notice: Subject to any disclaimer, the term of this patent is extended or adjusted under 35 U.S.C. 154(b) by 727 days.

(21) Appl. No.: 17/395,299

(22) Filed: Aug. 5, 2021

(65) Prior Publication Data
US 2022/0042781 A1 Feb. 10, 2022

Related U.S. Application Data

(60) Provisional application No. 63/062,217, filed on Aug. 6, 2020.

(51) Int. Cl.
*G01B 9/02* (2022.01)
*G01B 9/02091* (2022.01)
(Continued)

(52) U.S. Cl.
CPC ..... *G01B 9/02044* (2013.01); *G01B 9/02091* (2013.01); *G01N 21/359* (2013.01);
(Continued)

(58) Field of Classification Search
CPC ............ G01B 9/02044; G01B 9/02091; G01N 21/359; G01N 21/6486; G10K 2210/3213
See application file for complete search history.

(56) References Cited

U.S. PATENT DOCUMENTS 3,925,665 A * 12/1975 Robertson ............... G01T 1/115
250/337
6,016,192 A * 1/2000 Taylor ..................... H01J 43/30
356/229

(Continued)

FOREIGN PATENT DOCUMENTS

| WO | 2015/116939 A1 | 8/2015 |
| WO | 2015/116951 A2 | 8/2015 |
| WO | 2017/024145 A1 | 2/2017 |

OTHER PUBLICATIONS

Expanding the Dynamic Range of Fluorescence Assays through Single-Molecule Counting and Intensity Calibration, Lucas Smith, Manish Kohli, and Andrew M. Smith, Journal of the American Chemical Society, 2018, 140 (42), 13904-13912, DOI: 10.1021/jacs.8b08879 (Year: 2018).*

(Continued)

*Primary Examiner* — Kara E. Geisel
*Assistant Examiner* — Jonathon Cook
(74) *Attorney, Agent, or Firm* — Canon U.S.A., Inc. IP Division

(57) ABSTRACT

One or more devices, systems, methods, and storage mediums for performing imaging, for performing measurement(s), and/or for performing or controlling detector gain or photomultiplier tube gain using one or more imaging modalities are provided herein. Examples of applications include imaging, evaluating and diagnosing biological objects, such as, but not limited to, for Gastro-intestinal, cardio and/or ophthalmic applications, and being obtained via one or more optical instruments, such as, but not limited to, optical probes, catheters, capsules and needles (e.g., a biopsy needle). Devices, systems, methods, and storage mediums may include or involve a method, such as, but not limited to, for performing measurement(s) and/or controlling detector gain or photomultiplier gain, and may include (Continued)

or involve one or more imaging modalities, such as Optical Coherence Tomography and Fluorescence.

18 Claims, 14 Drawing Sheets

(51) Int. Cl.
  *G01N 21/359* (2014.01)
  *G01N 21/64* (2006.01)
  *A61B 8/08* (2006.01)
  *A61B 8/12* (2006.01)

(52) U.S. Cl.
  CPC ............ *G01N 21/6486* (2013.01); *A61B 8/08* (2013.01); *A61B 8/12* (2013.01)

(56) References Cited

U.S. PATENT DOCUMENTS

| | | | |
|---|---|---|---|
| 6,341,036 | B1 | 1/2002 | Tearney et al. |
| 6,583,424 | B2 * | 6/2003 | Staton ................ G01N 21/6452 250/252.1 |
| 7,447,408 | B2 | 11/2008 | Bouma et al. |
| 7,551,293 | B2 | 6/2009 | Yelin et al. |
| 7,796,270 | B2 | 9/2010 | Yelin et al. |
| 7,859,679 | B2 | 12/2010 | Bouma et al. |
| 7,872,759 | B2 | 1/2011 | Tearney et al. |
| 7,889,348 | B2 | 2/2011 | Tearney et al. |
| 8,045,177 | B2 | 10/2011 | Tearney et al. |
| 8,145,018 | B2 | 3/2012 | Shishkov et al. |
| 8,289,522 | B2 | 10/2012 | Tearney et al. |
| 8,838,213 | B2 | 9/2014 | Tearney et al. |
| 8,928,889 | B2 | 1/2015 | Tearney et al. |
| 9,254,089 | B2 | 2/2016 | Tearney et al. |
| 9,295,391 | B1 | 3/2016 | Tearney et al. |
| 9,332,942 | B2 | 5/2016 | Jaffer et al. |
| 9,415,550 | B2 | 8/2016 | Tearney et al. |
| 9,557,154 | B2 | 1/2017 | Tearney et al. |
| 2005/0219544 | A1 * | 10/2005 | Chan .................... A61B 5/0066 356/497 |
| 2007/0263171 | A1 * | 11/2007 | Ferguson ........... G01B 9/02044 351/206 |
| 2010/0092389 | A1 | 4/2010 | Jaffer |
| 2011/0176142 | A1 * | 7/2011 | Hacker ............... G01B 9/02009 356/479 |
| 2012/0101374 | A1 | 4/2012 | Tearney et al. |
| 2016/0228097 | A1 | 8/2016 | Jaffer et al. |
| 2017/0035281 | A1 | 2/2017 | Takeuchi et al. |
| 2017/0241763 | A1 * | 8/2017 | Wang ................. G01B 9/02078 |
| 2018/0003481 | A1 | 1/2018 | Yamada et al. |
| 2018/0017778 | A1 | 1/2018 | Ikuta et al. |
| 2018/0045501 | A1 | 2/2018 | Elmaanaoui |
| 2018/0271477 | A1 * | 9/2018 | Horiike ................ A61B 5/0035 |
| 2018/0348439 | A1 | 12/2018 | Yamada |
| 2019/0099079 | A1 * | 4/2019 | Yamada ............... A61B 5/0071 |
| 2020/0256661 | A1 | 8/2020 | Yamada |

OTHER PUBLICATIONS

X. Zhou, W. Geng, J. Li, Y. Wang, J. Ding, Y. Wang, An Ultraviolet-Visible and Near-Infrared-Responded Broadband NIR Phosphor and Its NIR Spectroscopy Application. Adv. Optical Mater. 2020, 8, 1902003. https://doi.org/10.1002/adom.201902003 (Year: 2020).*

Waters JC. Accuracy and precision in quantitative fluorescence microscopy. J Cell Biol. Jun. 29, 2009; 185(7):1135-48. doi: 10.1083/jcb.200903097. PMID: 19564400; PMCID: PMC2712964. (Year: 2009).*

Fluorescence Imaging principles and methods, Amersham Pharmacia Biotech Inc., 2000 (Year: 2000).*

Hamamatsu Photonics K. K., Stabilized Light Sources For Photomultiplier Tubes, L11494 and L11416, Dec. 2012, pp. 1-4.

* cited by examiner

DETECTOR OR PHOTOMULTIPLIER TUBE (PMT) GAIN CONTROL OVER TIME

CROSS-REFERENCE TO RELATED APPLICATION(S)

This application relates, and claims priority, to U.S. Patent Application Ser. No. 63/062,217, filed Aug. 6, 2020, the entire disclosure of which is incorporated by reference herein in its entirety.

FIELD OF THE INVENTION

The present disclosure relates generally to the field of optical imaging and more particularly to detectors and/or fiber optic rotary joints that may be used with one or more optical apparatuses, systems, methods (for using and/or manufacturing) and storage mediums, such as, but not limited to, fiber optic catheters, endoscopes and/or optical coherence tomography (OCT) and/or fluorescence apparatuses and systems, and methods and storage mediums, for use with same, to achieve structural compactness and high coupling efficiency. Examples of optical applications that may involve the use of one or more detectors, such as photo-multiplier tube(s) (PMTs) and/or a fiber optic rotary joint include imaging, evaluating and characterizing/identifying biological objects or tissue, such as, but not limited to, for gastro-intestinal, otolaryngologic, cardio and/or ophthalmic applications.

BACKGROUND OF THE INVENTION

Fiber optic catheters and endoscopes have been developed to access to internal organs. For example in cardiology, OCT (optical coherence tomography) has been developed to see depth resolved images of vessels with a catheter. The catheter, which may include a sheath, a coil and an optical probe, may be navigated to a coronary artery.

Optical coherence tomography (OCT) is a technique for obtaining high resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers are commonly used for OCT optical probes, and double clad fibers are also commonly used for fluorescence and/or spectroscopy.

Spectrally encoded endoscope (SEE) is an endoscope technology which uses a broadband light source, a rotating or oscillating grating and a spectroscopic detector to encode spatial information from a sample. When illuminating light to the sample, the light is spectrally dispersed along one illumination line, such that the dispersed light illuminates a specific position of the illumination line with a specific wavelength. When the reflected light from the sample is detected with a spectrometer, the intensity distribution is analyzed as the reflectance along the line where the wavelength encodes the spatial information. By rotating or oscillating the grating to scan the illumination line, a two-dimensional image of the sample is obtained.

In order to acquire cross-sectional images of tubes and cavities such as vessels, and/or esophagus and nasal cavities, the optical probe is rotated with a fiber optic rotary joint (FORJ). A FORJ is the interface unit that operates to rotate one end of a fiber and/or an optical probe. In general, a free space beam coupler is assembled to separate a stationary fiber and a rotor fiber inside the FORJ. Besides, the optical probe may be simultaneously translated longitudinally during the rotation so that helical scanning pattern images are obtained. This translation is most commonly performed by pulling the tip of the probe back along a guidewire towards a proximal end and, therefore, referred to as a pullback.

A multi-modality system such as an OCT, fluorescence, and/or spectroscopy system with an optical probe is developed to obtain multiple information at the same time. The multi-modality FORJ has a beam combiner for at least two beams with multiple wavelengths to couple into the probe. Generally, lenses are assembled to make collimated beams for both stationary and rotor fibers in the beam combiner. Further, the detected light may be collected in the same or in one or more additional fibers, and, if rotating, these additional fibers may structurally interfere with each other.

In a fluorescence (e.g., near-infrared auto-fluorescence (NIRAF), near-infrared fluorescence (NIRF), etc.) measurement system, performances of detectors, such as, but not limited to, photo-multiplier tube(s) (PMTs), degrade over time due to the lifespan or lifetime of the system and/or PMTs and/or due to damage. The detector/PMT is sensitive to input light intensity, and the lifetime or lifespan of the system and/or PMT changes at different input light intensity, gain setup, environment temperatures and/or humidity. For example, if the detector performance, such as gain, drops, the measurement accuracy of the system becomes worse.

However, it is difficult to access the detector/PMT to input stabilized light in the system. Even though the light source is integrated in the system, an optical switch is required when calibrating and acquiring signals. It especially is difficult to achieve the optical switch with low loss when the signals are delivered to the detectors/PMTs using multi-mode fibers. Also, typically the optical switch is expensive and big, so ideally no optical switch is desired.

Accordingly, it would be desirable to provide one or more detectors/PMTs for use in at least one optical device, assembly, or system to address one or more of the aforementioned inefficient and wasteful drawbacks, especially in a way that reduces or minimizes cost of manufacture, maintenance and/or use and/or in a way that achieves a device, assembly, or system that is able to calibrate gain of the one or more detectors/PMTs regularly, manually, or automatically without servicing/repairing of device, assembly, or system and/or without additional electrical components, such as stabilized light sources and optical switches, such that reliable NIRF and/or NIRAF measurements are achieved.

SUMMARY OF THE INVENTION

Accordingly, it is a broad object of the present disclosure to provide one or more detectors/PMTs that may be used with one or more optical apparatuses, systems, methods (for using and/or manufacturing) and storage mediums, such as, but not limited to, fiber optic catheters, endoscopes and/or optical coherence tomography (OCT) (or other imaging modality(ies), such as, but not limited to, NIRF, NIRAF, IVUS, etc.) apparatuses and systems, and methods and storage mediums, for use with same, to achieve structural compactness and high coupling efficiency. One or more additional objects of the present disclosure are to provide one or more methods of PMT/detector gain control over time when system initialization occurs.

One or more embodiments of the present disclosure may provide accurate fluorescence measurement results to user(s), and may prevent or avoid incorrect measurement results to degradation of a detector and/or PMT.

In one or more embodiments, an optical system may include: an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and to interfere, with each other, the interference light generating one or more interference patterns; one or more detectors that operate to continuously acquire the interference light and/or the one or more interference patterns to measure the interference or the one or more interference patterns between the combined or recombined light to obtain data for one or more imaging modalities; and one or more processors that operate to control a gain for the one or more detectors such that the optical system achieves reliable or consistent measurement(s) for the one or more imaging modalities and/or such that the optical system performs one or more calibrations for the one or more imaging modalities.

In one or more embodiments, one or more processors may operate to control the gain for the one or more detectors and/or operate to perform the one or more calibrations for the one or more imaging modalities by further operating to one or more of the following: (i) initializing the optical system; (ii) performing fluorescence calibration; (iii) performing or detecting a catheter disconnect mode, wherein a catheter is disconnected or determined to be disconnected from the optical system; (iv) performing connection of the catheter, performing the one or more calibrations, and performing or entering a standby mode; (v) performing or entering a Live Mode, the Live Mode operating to perform live view imaging and/or to obtain a real time image or images of the one or more imaging modalities to determine whether to acquire one or more images of the one or more imaging modalities; and/or (vi) performing and/or entering, automatically or manually, a record mode and/or a pullback mode, the record mode operating to record data, and the pullback mode operating to start or perform a pullback of a catheter of the optical system. In a case where the one or more processors perform the fluorescence calibration, the one or more processors may further operate to one or more of the following: (i) acquire one or more fluorescence signals, $FS_{BG-laser-off}$; (ii) turn on the light source or a laser signal from the light source and acquire one or more fluorescence signals, $FS_{BG-laser-on}$; (iii) calculate a background fluorescence signal, and determine whether the background fluorescence signal is in an adjustable range or a first set or in predetermined range and/or in an acceptable range or in a second set or predetermined range; (iv) in a case where the background fluorescence signal is not in an adjustable range or a set or predetermined first range and/or is not in an acceptable range or a set or predetermined second range, then the one or more processors cause a warning to be displayed on a display of the optical system and record the gain of the one or more detectors and the background fluorescence signal, and the optical system enters or goes to a fault state; (v) in the event that the background fluorescence signal is in an adjustable range or in a set or predetermined first range but is not in an acceptable range or is not in a set or predetermined second range, then the one or more processors adjust a fluorescence detector sensitivity of the one or more detectors to use feedback circuits or algorithms to maintain the background fluorescence signal; and/or (vi) in the event that the background fluorescence signal is in an adjustable range or in a set or predetermined first range and is in an acceptable range or in a set or predetermined second range, then the one or more processors record the gain of the one or more detectors and the fluorescence signal, and returns the system to a standby mode and/or the catheter disconnect mode.

In one or more embodiments, one or more of the following may exist or may occur: (i) the one or more detectors include or comprise one or more of the following: photodiodes, Photomultiplier tube(s) (PMTs), line scan camera(s), and/or multi-array camera(s); (ii) in a case where the one or more processors use feedback circuits or algorithms, the one or more processors operate to adjust the gain of the one or more detectors with a supplied control voltage, and operate to turn off the light source or the laser signal of the light source, and then start the fluorescence calibration; and/or (iii) the one or more imaging modalities includes one or more of the following: Optical Coherence Tomography (OCT), single modality OCT, multi-modality OCT, swept source OCT, optical frequency domain imaging (OFDI), intravascular ultrasound (IVUS), another lumen image(s) modality, near-infrared spectroscopy, near-infrared fluorescence (NIRF), near-infrared auto-fluorescence (NIRAF), and an intravascular imaging modality. One or more of the following may exist or may occur: (i) in a case where the one or more processors perform the initialization of the optical system and perform the fluorescence calibration, the one or more processors operate to calibrate the gain or a control of the one or more detectors by or to keep signals constant; (ii) in a case where the one or more processors perform the initialization of the optical system and perform the fluorescence calibration, the one or more processors operate to calibrate the gain or a control of the one or more detectors by or to keep signals constant, the optical system being without catheter or probe connection(s); (iii) the one or more processors use a lookup value or values, and such value(s) may be recorded or may record an output in a log or logs; (iv) the one or more processors acquire the one or more fluorescence signals, $FS_{BG-laser-off}$, while the light source or the laser signal of the light source is off; (v) the one or more processors further operate to average the one or more fluorescence signals, $FS_{BG-laser-off}$, to minimize or reduce one or more random noises; and/or (vi) one or more processors further operate to average the one or fluorescence signals, $FS_{BG\text{-}laser\text{-}on}$, to minimize or reduce one or more random noises.

In one or more embodiments, one or more processors may operate to calculate the background fluorescence signal, $FS_{BG\text{-}laser\text{-}on}-FS_{BG\text{-}laser\text{-}off}$, and then evaluate whether the background fluorescence signal is one of the following: (i) in the adjustable range or the first set or predetermined range and/or in the acceptable range or in the second set or predetermined range; (ii) not in the adjustable range or in the set or predetermined first range and/or not in the acceptable range or in the set or predetermined second range; (iii) in the adjustable range or in the set or predetermined first range but not in the acceptable range or not in the set or predetermined second range; or (iv) in the adjustable range or in the set or predetermined first range and in the acceptable range or in the set or predetermined second range. In one or more embodiments, the one or more processors may further operate to determine whether accurate or correct measurements are obtainable based on the evaluation of the background fluorescence signal being in the adjustable range or in the set or predetermined first range and in the acceptable range or in the set or predetermined second range or whether incorrect or inaccurate measurements are obtainable otherwise such that the one or more processors and/or the optical system provide the warnings and/or calibrate the sensitivity of the one or more detectors to control the gain with a feedback loop.

One or more embodiments of the present disclosure may include a phosphor that operates to produce or sent the background fluorescence signal, wherein the one or more processors further operate to obtain the background fluorescence signal from the phosphor and/or further operate to use the obtained background fluorescence signal to analyze or evaluate a sensitivity and/or a gain degradation of a fluorescence detector of the one or more detectors. In one or more embodiments, one or more of the following may exist or may occur: (i) the phosphor emits emissions having wavelengths longer than a light or excitation light from the light source in a case where the phosphor is excited by the light or excitation light from the light source; (ii) the emissions of the phosphor are one or more of the following: Raman, fluorescence, and/or auto-fluorescence; and/or (iii) in a case where the emissions are Raman emissions, the Raman scattering lights do not decay over time so that the Raman scattering lights operate to be used for calibration of the one or more detectors.

In one or more embodiments, one or more of the following may exist or may occur: (i) the adjustable range or the set or predetermined first range is one or more of the following: a default range obtained by calculating the background fluorescence signal, a default range obtained from a log file, a range automatically set by the system, a range set or adjusted by the user, two times a target value at one end of the adjustable range or the set or predetermined first range and 0.5 times or half the size of the target value at another end of the adjustable range or the set or predetermined first range, a range having a first target value at one end of the adjustable range or the set or predetermined first range and having a second target value at another end of the adjustable range or the set or predetermined first range, based on prior values or ranges used for the adjustable range or the set or predetermined first range, a range with positive values; (ii) the acceptable range or the set or predetermined second range is one or more of the following: a default range obtained by calculating the background fluorescence signal, a default range obtained from a log file, a range automatically set by the system, a range set or adjusted by the user, two times a target value at one end of the acceptable range or the set or predetermined second range and 0.5 times or half the size of the target value at another end of the acceptable range or the set or predetermined second range, a range having a first target value at one end of the acceptable range or the set or predetermined second range and having a second target value at another end of the acceptable range or the set or predetermined second range, based on prior values or ranges used for the acceptable range or the set or predetermined second range, and/or a range with positive values; (iii) the background fluorescence signal is in the adjustable range or the set or predetermined first range in a case where the background fluorescence signal is one or more of the following: within a set distance from a target value, within +/−10% of the target value, +/−5% of the target value, within +/−5-10% of the target value, a positive value, is a value equaling or being between a first value at one end of the adjustable range or of the set or predetermined first range and a second value at another end of the adjustable range or of the set or predetermined first range, and/or about the same as one or more previously used background fluorescence signals determined to be in the adjustable range or the set or predetermined first range; and/or (iv) the background fluorescence signal is in the acceptable range or the set or predetermined second range in a case where the background fluorescence signal is one or more of the following: within a set distance from a target value, within +/−10% of the target value, +/−5% of the target value, within +/−5-10% of the target value, a positive value, is a value equaling or being between a first value at one end of the acceptable range or of the set or predetermined second range and a second value at another end of the acceptable range or of the set or predetermined second range, and/or about the same as one or more previously used background fluorescence signals determined to be in the acceptable range or the set or predetermined second range.

In one or more embodiments, (i) in a case where the optical system is in the standby mode or the catheter disconnect mode, the optical system may be waiting for, and/or the one or more processors may operate to detect, a connection of a catheter to the optical system; and/or (ii) in a case where the optical system and/or the one or more processors detect a catheter disconnection, the optical system may enter the standby mode and/or the catheter disconnect mode.

In one or more embodiments, in a case where a catheter is connected to the optical system, the optical system and/or the one or more processors of the optical system may operate to perform the one or more calibrations automatically and/or manually, and the one or more calibrations may include one or more of the following: (i) the fluorescence calibration, (ii) a z-offset calibration for Optical Coherence Tomography (OCT) to adjust the reference arm where the one or more imaging modalities includes OCT, and/or (iii) catheter background subtraction for fluorescence images where the one or more imaging modalities includes fluorescence, near-infrared fluorescence (NIRF), and/or near-infrared auto fluorescence (NIRAF).

In one or more embodiments, a device or system may further include a fiber optic rotary joint (FORJ) including: a beam combiner; a rotor that operates to rotate and that includes a common optical fiber connected to or part of the beam combiner; and a stator that operates to be stationary in the fiber optic rotary joint and that includes at least two optical fibers, a first of the at least two optical fibers operating to guide at least the first light and being connected to or part of the beam combiner and a second of the at least two optical fibers operating to guide a third light and being connected to or part of the beam combiner, wherein the beam combiner operates to combine the first and third lights from the at least two optical fibers such that the combined light couples, or substantially couples, into a core of the common optical fiber. In one or more embodiments, the combined light may operate to irradiate the sample, and the FORJ may include at least one dichroic filter to separate the combined light into OCT light to be transmitted to the at least one detector and into fluorescent light to be transmitted to at least another detector. In one or more embodiments, the system may further include one or more of the following: (i) at least two light sources, a first of the at least two light sources operating to produce the first light, which is an OCT light, and a second of the at least two light sources operating to produce the third light, which is an excitation light; and/or (ii) at least one of a motor and a processor that operates to rotate the rotor of the FORJ.

In one or more embodiments, an optical system for one or more imaging modalities may include: a passive emission source that operates to receive a first light from a light source and that operates to generate or create a second light collected from the passive emission source; a beam combiner and/or separator that operates to separate the first light and the second light; and one or more detectors, wherein: the second light is propagated to the one or more detectors, the second light has a longer wavelength than a wavelength of the first light, and the optical system acquires the second light before performing or taking one or more measurements. In one or more embodiments, the passive emission source may be a phosphor.

One or more embodiments may further include one or more processors that operate to one or more of the following: (i) record data for the acquired second light into a log file; (ii) analyze the acquired second light to compare one or more set or predetermined values; (iii) issues or transmits one or more warning messages in a case where the second acquired light is out of range of a predetermined or set range; (iv) provides feedback to adjust a sensitivity or a gain of the one or more detectors to maintain the second light from the passive emission source to be within the predetermined or set range; and/or (v) evaluate or analyze the acquired second light and/or the one or more detectors before an attachable optical probe or catheter is connected to the optical system. In one or more embodiments, the detected second light may include a wavelength of 400 nm-900 nm or of 620 nm-850 nm, and/or the detected second light may be a fluorescence light and/or an auto-fluorescence light such that the first light is an excitation light of the fluorescence light and/or the auto-fluorescence light.

In one or more embodiments, one or more of the following may exist or may occur: (i) the optical system further comprises a removably attachable optical probe or an attachable optical probe; and/or (ii) the optical system further comprises a removably attachable optical probe or an attachable optical probe, wherein the optical probe is made of fiber with or having at least two clads.

In one or more embodiments, one or more of the following may exist or may occur: (i) the one or more detectors include or comprise one or more of the following: photodiodes, Photomultiplier tube(s) (PMTs), line scan camera(s), and/or multi-array camera(s); and/or (ii) and/or the one or more imaging modalities includes one or more of the following: Optical Coherence Tomography (OCT), single modality OCT, multi-modality OCT, swept source OCT, optical frequency domain imaging (OFDI), intravascular ultrasound (IVUS), another lumen image(s) modality, near-infrared spectroscopy, near-infrared fluorescence (NIRF), near-infrared auto-fluorescence (NIRAF), and an intravascular imaging modality.

One or more methods for controlling an optical system are provided herein. In one or more embodiments, a method for controlling an optical system having an interference optical system that operates to generate interference light and one or more interference patterns, and one or more detectors that operate to continuously acquire the interference light and/or the one or more interference patterns to measure the interference or the one or more interference patterns to obtain data for one or more imaging modalities, may include: controlling a gain for the one or more detectors such that the optical system achieves reliable or consistent measurement(s) for the one or more imaging modalities and/or such that the optical system performs one or more calibrations for the one or more imaging modalities. In one or more embodiments, a method may further include one or more of the following: (i) initializing the optical system; (ii) performing fluorescence calibration; (iii) performing or detecting a catheter disconnect mode, wherein a catheter is disconnected or determined to be disconnected from the optical system; (iv) performing connection of the catheter, performing the one or more calibrations, and performing or entering a standby mode; (v) performing or entering a Live Mode, the Live Mode operating to perform live view imaging and/or to obtain a real time image or images of the one or more imaging modalities to determine whether to acquire one or more images of the one or more imaging modalities; and/or (vi) performing and/or entering, automatically or manually, a record mode and/or a pullback mode, the record mode operating to record data, and the pullback mode operating to start or perform a pullback of a catheter of the optical system. In one or more embodiments, a method may further include one or more of the following: (i) acquiring one or more fluorescence signals, $FS_{BG\text{-}laser\text{-}off}$; (ii) turning on the light source or a laser signal from the light source and acquiring one or more fluorescence signals, $FS_{BG\text{-}laser\text{-}on}$; (iii) calculating a background fluorescence signal, and determining whether the background fluorescence signal is in an adjustable range or in a first set or predetermined range and/or in an acceptable range or in a second set or predetermined range; (iv) in a case where the background fluorescence signal is not in an adjustable range or in a set or predetermined first range and/or is not in an acceptable range or in a set or predetermined second range, then displaying a warning on a display of the optical system and recording the gain of the one or more detectors and the background fluorescence signal, and having the optical system enter or go to a fault state; (v) in the event that the background fluorescence signal is in an adjustable range or in a set or predetermined first range but is not in an acceptable range or is not in a set or predetermined second range, then adjusting a fluorescence detector sensitivity of the one or more detectors to use feedback circuits or algorithms to maintain the background fluorescence signal; and/or (vi) in the event that the background fluorescence signal is in an adjustable range or in a set or predetermined first range and is in an acceptable range or in a set or predetermined second range, then recording the gain of the one or more detectors and the fluorescence signal, and returning the system to a standby mode and/or the catheter disconnect mode.

In accordance with one or more embodiments of the present disclosure, apparatuses and systems, and methods and storage mediums for use with one or more embodiments of a detector/PMT may operate to characterize biological objects, such as, but not limited to, blood, mucus, tissue, etc.

In accordance with one or more aspects of the present disclosure, at least one embodiment of a detector/PMT in an apparatus or system may relate to forward and side views or imaging. Additionally or alternatively, one or more embodiments of a detector/PMT in an apparatus or system may relate to using a photo diode. At least one embodiment may obtain one or more types of images (e.g., SEE, OCT, NIRF, NIRAF, etc.).

One or more embodiments of the present disclosure may be used in clinical application(s), such as, but not limited to, intervascular imaging, atherosclerotic plaque assessment, cardiac stent evaluation, balloon sinuplasty, sinus stenting, arthroscopy, ophthalmology, ear research, veterinary use and research, etc.

In accordance with at least another aspect of the present disclosure, the detector(s)/PMT(s) and one or more technique(s) discussed herein may be employed to reduce the cost of at least one of manufacture and maintenance of the detector(s)/PMT(s) in one or more devices, systems and storage mediums by reducing or minimizing a number of optical components in an interference optical system, such as an interferometer and/or such as using other light sources including LEDs (e.g., when sensitivity is sufficient and/or meets a predetermined condition, threshold or requirement) to cut down cost.

According to other aspects of the present disclosure, one or more additional devices, one or more systems, one or more methods and one or more storage mediums using, or for use with, one or more detectors and/or PMTs are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, optical systems, methods and storage mediums for imaging using one or more detectors and/or PMTs, and one or more methods of performing measurements, are disclosed herein.

Figure 1:
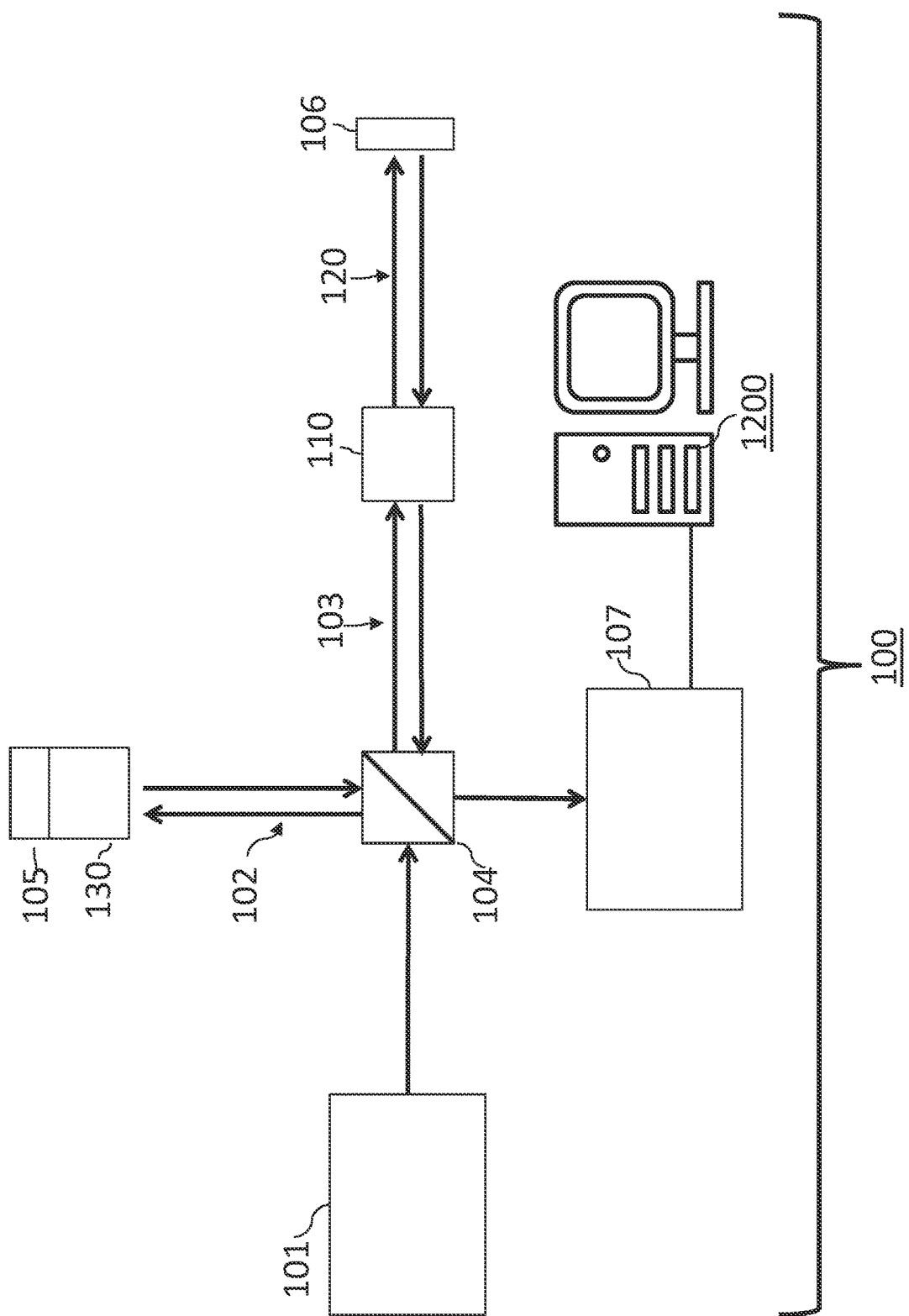
FIG. 1 is a diagram showing an embodiment of a system which can utilize one or more detectors and/or PMTs, and/or measurement method(s), in accordance with one or more aspects of the present disclosure.

Turning now to the details of the figures, FIG. 1 shows an OCT system 100 (as referred to herein as "system 100" or "the system 100") which operates to utilize an OCT technique with optical probe applications in accordance with one or more aspects of the present disclosure. The system 100 comprises a light source 101, a reference arm 102, a sample arm 103, a splitter 104 (also referred to herein as a "beam splitter"), a reference mirror (also referred to herein as a "reference reflection") 105, and one or more detectors 107. The system 100 may include a phase shift device or unit 130. In one or more embodiments, the system 100 may include a patient interface device or unit ("PIU") 110 and a catheter 120 (as diagrammatically shown in FIGS. 1-4), and the system 100 may interact with a sample 106 (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the splitter 104 and the reference mirror 105.

The light source 101 operates to produce a light to the splitter 104, which splits the light from the light source 101 into a reference beam passing into the reference arm 102 and a sample beam passing into the sample arm 103. The beam splitter 104 is positioned or disposed at an angle to the reference mirror 105, the one or more detectors 107 and to the sample 106. The reference beam goes through the phase shift unit 130 (when included in a system, as shown in the system 100), and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200, 1200' (shown in FIG. 12 or FIG. 13, respectively, discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

The light source 101 may include a plurality of light sources or may be a single light source. The light source 101 generates broadband laser lights in one or more embodiments. The light source 101 may include one or more of a laser, an organic Light-Emitting Diode (OLED), a Light-Emitting Diode (LED), a halogen lamp, an incandescent lamp, supercontinuum light source pumped by a laser, and/or a fluorescent lamp. The light source 101 may be any light source that provides light which can then be split up into at least three bands in which each band is further dispersed to provide light which then used to for spectral encoding of spatial information. The light source 101 may be fiber coupled or may be free space coupled to the other components of the system or systems discussed herein, such as, but not limited to, the system 100, the system 100', the system 100a, the system 100", the system 100''', any other system discussed herein, etc. In one or more embodiments, multiple light sources 101 may be provided where at least one light source 101 is an OCT light source and at least another light source 101 is a fluorescence light source.

In accordance with at least one aspect of the present disclosure, a feature of OCT systems is implemented using fiber optics. As aforementioned, one application of an OCT technique of the present disclosure is to use OCT and/or fluorescence (or one or more imaging modalities) with a catheter 120 as schematically shown in FIGS. 1-4.

In one or more embodiments of the present disclosure, fiber optic catheters and endoscopes have been developed to provide access to internal organs. For example in the field of cardiology, OCT (optical coherence tomography), white light back-reflection, NIRS (near infrared spectroscopy), and fluorescence technology have been developed to see structural and/or molecular images of vessels with a catheter (although one or more other imaging modalities may be used, additionally or alternatively, in one or more embodiments of the present disclosure). The catheter, which may comprise a sheath and an optical probe, may be navigated to a coronary artery.

One or more embodiments may acquire cross-sectional images of tubes and cavities, such as, but not limited to, vessels, the esophagus, a nasal cavity, or other types of tubes and cavities, the optical probe (e.g., the probe 120) may be rotated with a fiber optic rotary joint (FORJ) (such as, but not limited to, a FORJ 306, a FORJ 306', any other rotary joint discussed herein, etc.). In addition, the optical probe (e.g., the probe 120) may be simultaneously translated longitudinally during the rotation so that helical scanning pattern images may be obtained. This translation may be performed by pulling the tip of the probe (e.g., the probe 120) back towards a proximal end, and this process is, therefore, referred to as a pullback.

Imaging of arteries (e.g., coronary arteries) by one or more intravascular OCT and fluorescence systems is described in one or more embodiments of the present disclosure. One or more embodiments of such systems may obtain reliable, regularly calibrated florescence signals.

Figure 2A:
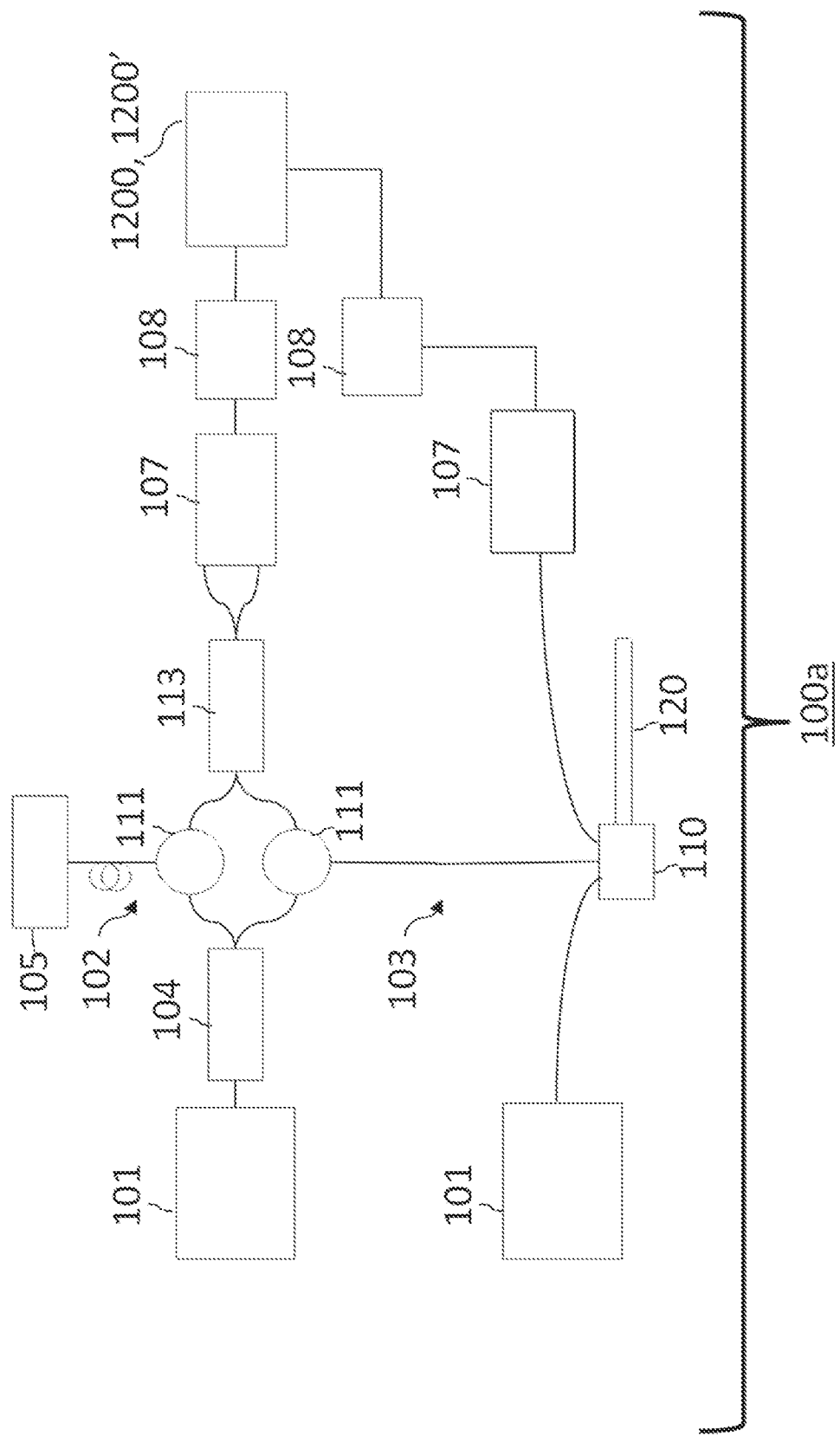
FIGS. 2A-2B are diagrams showing embodiments of one or more systems which can utilize one or more detectors and/or PMTs, and/or measurement method(s), in accordance with one or more aspects of the present disclosure.

FIG. 2A shows at least one embodiment of a system 100a which includes OCT and fluorescence sub-systems. In one or more embodiments, the OCT sub-system includes a light source, such as the light source 101, a splitter (such as the splitter 104; another type of deflecting or deflection device discussed below may be used in place of the splitter 104), one or more circulators 111, a reference reflection (such as the reference reflection 105), a combiner (such as the combiner 113), and at least one detector (such as the at least one detector 107). The OCT sub-system may be connected to, and include, a patient interface unit, such as the PIU 110, and the catheter 120 to expose a sample, such as the sample 106, to light and receive information in response thereto. In one or more embodiments, the fluorescence sub-system may include a light source for fluorescence (such as the second light source 101 shown in FIG. 2A) and at least one detector (such as the second at least one detector 107 shown in FIG. 2A). The fluorescence sub-system, including, but not limited to, the second light source 101 and the second at least one detector 107, may also be connected to (see FIG. 2A), and/or include, a patient interface unit, such as the PIU 110, and the catheter 120 to expose a sample, such as the sample 106, to fluorescent light and receive information in response thereto. For example, in at least one embodiment, an OCT light with a wavelength of around 1.3 um from a light source (such as the light source 101 of the OCT sub-system) may be delivered and split into a reference arm (e.g., the reference arm 102) and a sample arm (e.g., the sample arm 103) with a splitter (e.g., the splitter 104). A reference beam is reflected from a reference mirror (e.g., the reference reflection 105) in the reference arm (e.g., the reference arm 102) while a sample beam is reflected or scattered from a sample through a PIU (patient interface unit) (such as the PIU 110) and a catheter (e.g., the catheter 120) in the sample arm (e.g., the sample arm 103). Both beams combine at a combiner (e.g., the splitter 104 in FIG. 1, the combiner 113 in FIG. 2A, etc.) and generate interference patterns. The output of the interferometer is detected with detectors (e.g., the at least one detector 107 shown in FIG. 1, the at least one detector 107 of the OCT sub-system shown in FIG. 2A, etc.) such as photodiodes, multi-array cameras, PMTs, etc. Then signals are transferred to a computer (e.g., the computer 1200 as shown in FIGS. 1-2A and 12, the computer 1200' of FIG. 2A, FIG. 13, etc.) to perform signal processing. The interference patterns are generated only when the path length of the sample arm (e.g., the sample arm 103) matches that of the reference arm (e.g., the reference arm 102) to within the coherence length of the light source (e.g., the light source 101 of FIG. 1, the light source 101 of the OCT sub-system of FIG. 2A, etc.). In one or more embodiments, the one or more detectors 107 of the OCT sub-system may send the signal(s) to a first data acquisition unit or processor 108, and the first data acquisition unit or processor 108 may send the signal(s) to the computer (e.g., the computer 1200, the computer 1200', any other computer discussed herein, etc.). In one or more embodiments, the one or more detectors 107 of the fluorescence sub-system may send the signal(s) to a second data acquisition unit or processor 108, and the second data acquisition unit or processor 108 may send the signal(s) to the computer (e.g., the computer 1200, the computer 1200', any other computer discussed herein, etc.)

In one or more embodiments, although not limited to double clad fiber(s), fiber(s) of the PIU (e.g., the PIU 110) and the catheter (e.g., the probe of the catheter 120) may be made of a double clad fiber (DCF). OCT light may illuminate a sample (e.g., the sample 106) through the DCF (e.g., through the core of the DCF), and scattered light from the sample (e.g., the sample 106) may be collected and delivered back to the circulator (e.g., the circulator 11, the lower or second circulator in in FIG. 2A, a circulator of an OCT interferometer, the circulator in of the OCT sub-system, etc.) via the PIU (e.g., the PIU 110) and may be combined with the reference beam at a combiner (e.g., the combiner 113) to generate one or more interference patterns. The output of an OCT interferometer and/or the combiner 113 may be detected with the one or more OCT detectors (e.g., the one or more detectors 107), such as, but not limited to, photodiodes, multi-array cameras, PMTs, etc. Signals may be transferred to a computer (e.g., the computer 1200, the computer 1200', any other computer discussed herein, etc.) to perform signal processing to generate OCT image(s). The interference patterns may be generated when the path length of the sample arm (e.g., the sample arm 103) matches that of the reference arm (e.g., the reference arm 102) to within the coherence length of the light source (e.g., the light source 101, the light source 101 of the OCT sub-system, etc.).

An excitation light with a wavelength (e.g., any predetermined wavelength visible to infrared (IR)), for example, 0.633 um from a light source (e.g., the light source 101 of the fluorescence sub-system of FIG. 2A) or 0.635 um from the light source (e.g., the light source 101 of the fluorescence sub-system of FIG. 2A) may be delivered to the sample (e.g., the sample 106) through the PIU (e.g., the PIU 110) and the catheter (e.g., the catheter 120). The sample (e.g., the sample 106) may emit auto-fluorescence light with broadband wavelengths of, for example, 0.633 um-0.80 um by the excitation light. By way of another example, the sample (e.g., the sample 106) may emit auto-fluorescence light with broadband wavelengths of 0.65 um-0.90 um. The auto-fluorescence light may be collected with the catheter (e.g., the catheter 120 of FIG. 2A) and delivered to detectors (e.g., the detector(s) 107 of the fluorescence sub-system of FIG. 2A, a fluorescence detector(s) such as a photo-multiplier tube (PMT) or tubes (PMTs), etc.) via the PIU (e.g., the PIU 110). Other wavelengths, in the visible and NIR are also contemplated. In one or more embodiments, the patient interface unit (PIU; e.g., the PIU 110 as further discussed below) may include or comprise a free space beam combiner so that the excitation light couples into a common DCF or other possible/useful fiber with OCT. The excitation light may be illuminated to the sample (e.g., the sample 106) from a distal end of the optical probe in the catheter (e.g., the catheter or the probe 120).

Figure 2B:
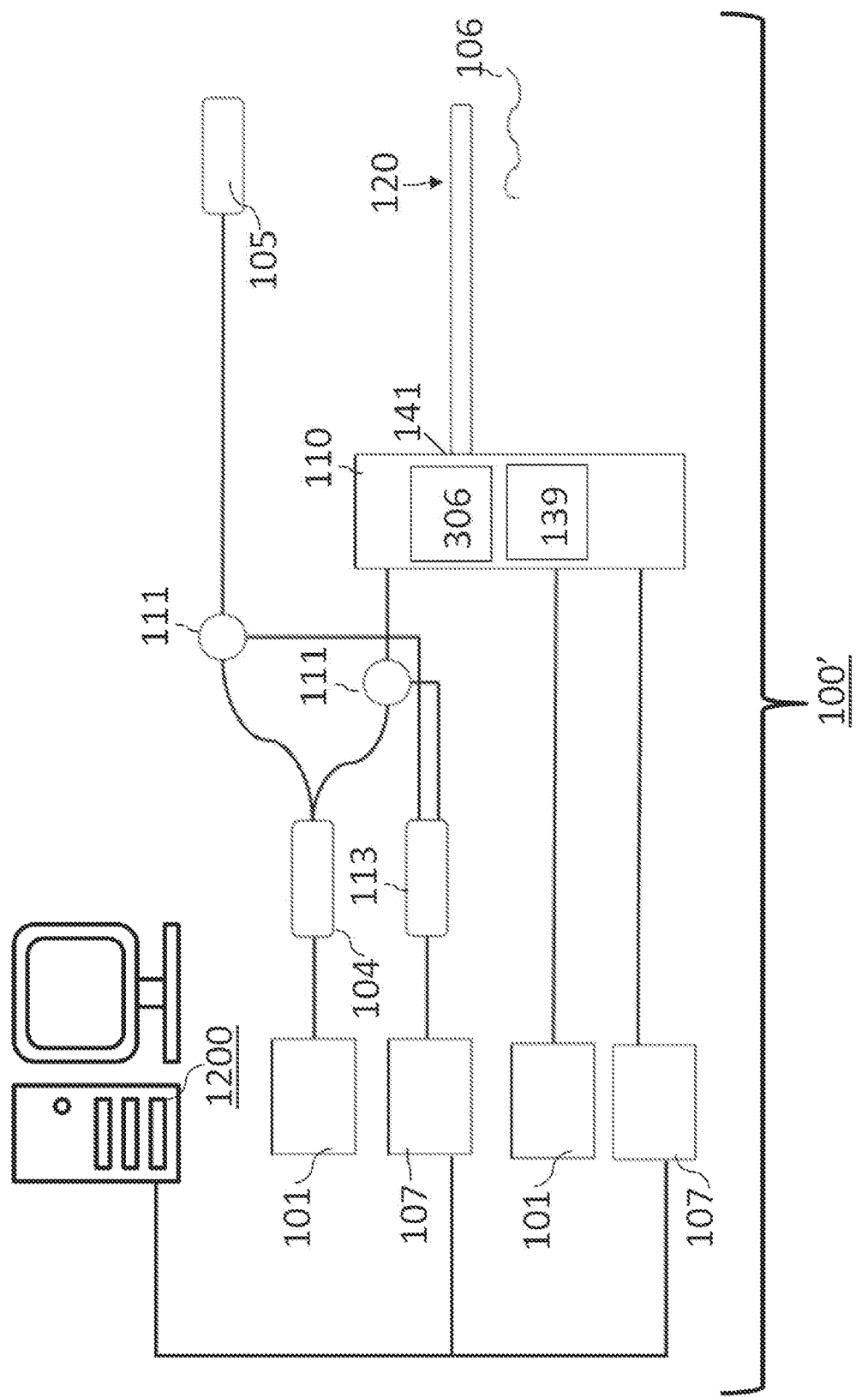
Figure 11:
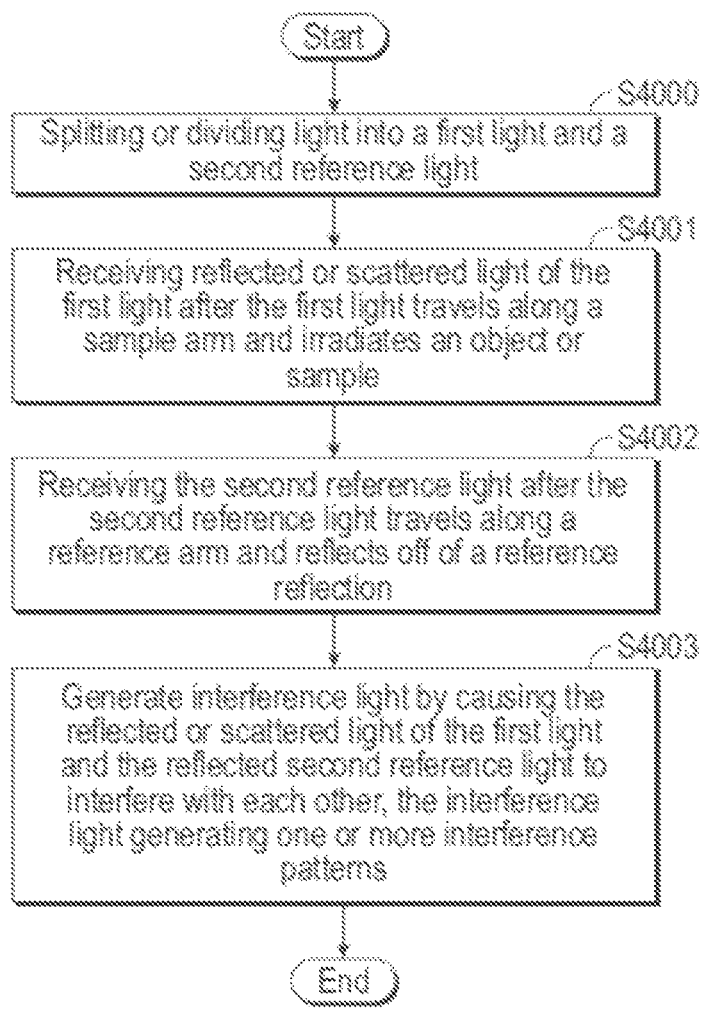
FIG. 11 is a flow diagram illustrating at least one method embodiment of performing an imaging feature, function, or technique that may be used with one or more detectors/PMTs, and/or one or more measurement techniques, in accordance with one or more aspects of the present disclosure.

FIG. 2B shows at least one embodiment of a system 100' which includes OCT and fluorescence sub-systems. In one or more embodiments, the OCT sub-system includes a light source, such as the light source 101, a splitter (such as the splitter 104; another type of deflecting or deflection device discussed below may be used in place of the splitter 104), one or more circulators 111, a reference reflection (such as the reference reflection 105), a combiner (such as the combiner 113), and at least one detector (such as the at least one detector 107). The OCT sub-system may be connected to, and include, a patient interface unit, such as the PIU 110, and the catheter 120 to expose a sample, such as the sample 106, to light and receive information in response thereto. In one or more embodiments, the fluorescence sub-system may include a light source for fluorescence (such as the second light source 101 shown in FIG. 2B) and at least one detector (such as the second at least one detector 107 shown in FIG. 2B). The fluorescence sub-system, including, but not limited to, the second light source 101 and the second at least one detector 107, may also be connected to (see FIG. 2B), and/or include, a patient interface unit, such as the PIU 110, and the catheter 120 to expose a sample, such as the sample 106, to fluorescent light and receive information in response thereto. For example, in at least one embodiment, an OCT light with a wavelength of around 1.3 um from a light source (such as the light source 101 of the OCT sub-system) is delivered and split into a reference arm (e.g., the reference arm 102) and a sample arm (e.g., the sample arm 103) with a splitter (e.g., the splitter 104). A reference beam is reflected from a reference mirror (e.g., the reference reflection 105) in the reference arm (e.g., the reference arm 102) while a sample beam is reflected or scattered from a sample through a PIU (patient interface unit) (such as the PIU 110) and a catheter (e.g., the catheter 120) in the sample arm (e.g., the sample arm 103). Both beams combine at a combiner (e.g., the splitter 104 in FIG. 1, the combiner 113 in FIG. 2B, etc.) and generate interference patterns. The output of the interferometer is detected with detectors (e.g., the at least one detector 107 shown in FIG. 1, the at least one detector 107 of the OCT sub-system shown in FIG. 2B, etc.) such as photodiodes or multi-array cameras. Then signals are transferred to a computer (e.g., the computer 1200 as shown in FIGS. 1-2 and 11, the computer 1200' of FIG. 12, etc.) to perform signal processing. The interference patterns are generated only when the path length of the sample arm (e.g., the sample arm 103) matches that of the reference arm (e.g., the reference arm 102) to within the coherence length of the light source (e.g., the light source 101 of FIG. 1, the light source 101 of the OCT sub-system of FIG. 2B, etc.).

An excitation light with a wavelength (e.g., any predetermined wavelength visible to infrared (IR)), for example, 0.633 um from a light source (e.g., the light source 101 of the fluorescence sub-system of FIG. 2B) is delivered to the sample (e.g., the sample 106) through the PIU (e.g., the PIU 110) and the catheter (e.g., the catheter 120). The sample (e.g., the sample 106) emits auto-fluorescence light with broadband wavelengths of, for example, 0.633 um-0.80 um by the excitation light. The auto-fluorescence light is collected with the catheter (e.g., the catheter 120 of FIG. 2B) and delivered to detectors (e.g., the detector(s) 107 of the fluorescence sub-system of FIG. 2B) via the PIU (e.g., the PIU 110). By way of another example, the sample (e.g., the sample 106) may emit auto-fluorescence light with broadband wavelengths of 0.65 um-0.90 um. The auto-fluorescence light may be collected with the catheter (e.g., the catheter 120 of FIG. 2B) and delivered to detectors (e.g., the detector(s) 107 of the fluorescence sub-system of FIG. 2B, a fluorescence detector(s) such as a photo-multiplier tube (PMT) or tubes (PMTs), etc.) via the PIU (e.g., the PIU 110). Other wavelengths, in the visible and NIR are also contemplated. The embodiment of FIG. 2B may include one or more of the aforementioned features of FIG. 2A, and such features are not further discussed herein as a result.

Figure 3:
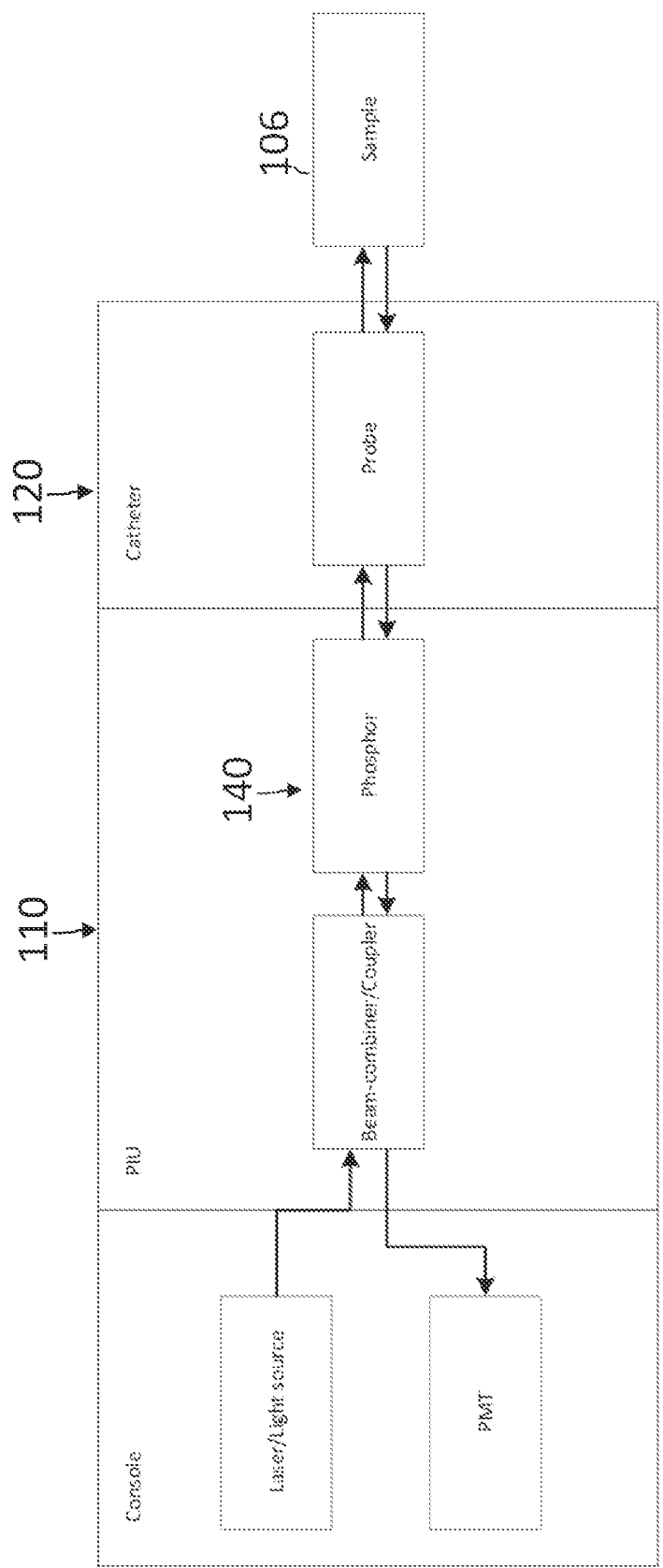
FIG. 3 is a diagram showing at least one embodiment of a system which may utilize phosphor in accordance with one or more aspects of the present disclosure.

FIG. 3 shows diagrammatically that one or more embodiments of the present disclosure may include a phosphor (e.g., a phosphor 140 as shown in FIG. 3). A phosphor (e.g., the phosphor 140 of FIG. 3) may be placed in a rotating double clad fiber or any other fiber that may be used for a PIU (e.g., the PIU 110) and/or the catheter (e.g., the catheter 120). A phosphor (e.g., the phosphor 140) may emit emissions, which have wavelengths that are longer than those of the excitation light, when the phosphor is excited by the excitation light. The emissions of the phosphor (e.g., the phosphor 140) may be Raman, fluorescence, and/or auto-fluorescence (and/or other types of emissions as discussed herein). The Raman scattering lights does not decay over time, such as photo-bleaching, so the Raman scattering lights may be used for PMT calibration.

Figure 4:
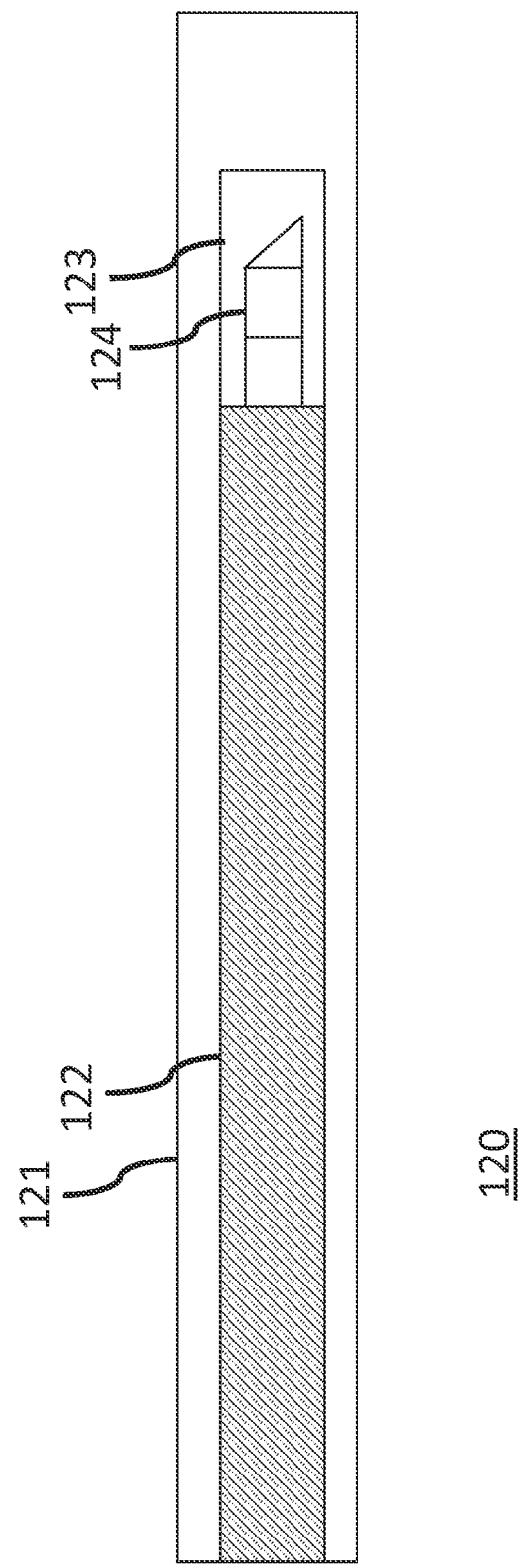
FIG. 4 is a diagram of an embodiment of a catheter that may used with at least one embodiment of a fiber optic rotary joint in accordance with one or more aspects of the present disclosure.

FIG. 4 shows an embodiment of the catheter 120 including a sheath 121, a coil 122, a protector 123 and an optical probe 124. As shown schematically in FIGS. 1-3, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, an inner surface of hollow organs such as vessels, etc. For example, fiber optic catheters and endoscopes may reside in the sample arm (such as the sample arm 103 as shown in FIG. 1) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

In one or more embodiments, the optical probe (e.g., the probe 124 of the catheter 120) may comprise or include an optical fiber connector, an optical fiber, and a distal lens. The optical fiber connector is used to engage with the PIU (e.g., the PIU 110). The optical fiber operates to deliver light to the distal lens. The distal lens operates to shape the optical beam and to illuminate light to the sample (e.g., the sample 106), and to collect light from the sample (e.g., the sample 106) efficiently. The double clad fiber may be used to transmit and/or collect OCT light through the core and to collect Raman and/or fluorescence light from sample (e.g., the sample 106) through the clad. The lens may be used for focusing and collecting light to and/or from the sample (e.g., the sample 106). The scattered light through the clad may be relatively higher than that through the core in a case or instance where a size of the core is smaller or much smaller than a size of the clad.

In at least one embodiment, there is a mirror (e.g., mirror 504 of FIGS. 5-6 as discussed below) at the distal end so that the light beam is deflected outward. In at least one embodiment, the optical probe 124 may comprise or include a fiber connector at a proximal end, a double clad fiber, and a lens at a distal end. The fiber connector may be connected with the PIU 110. The double clad fiber (see e.g., double clad fiber 506 of FIGS. 5-6 as discussed below) may be used to deliver both OCT and fluorescence lights. The lens (see e.g., GRIN lens 501b shown in FIG. 5 as discussed below) may be used for focusing and collecting lights to and/or from the sample (e.g., the sample 106). The double clad fiber may be used to transmit and/or collect OCT light through the core and to collect Raman and/or fluorescence light from sample (e.g., the sample 106) through the clad. The lens may be used for focusing and collecting light to and/or from the sample (e.g., the sample 106). The scattered light through the clad may be relatively higher than that through the core in a case or instance where a size of the core is smaller or much smaller than a size of the clad.

Figure 5:
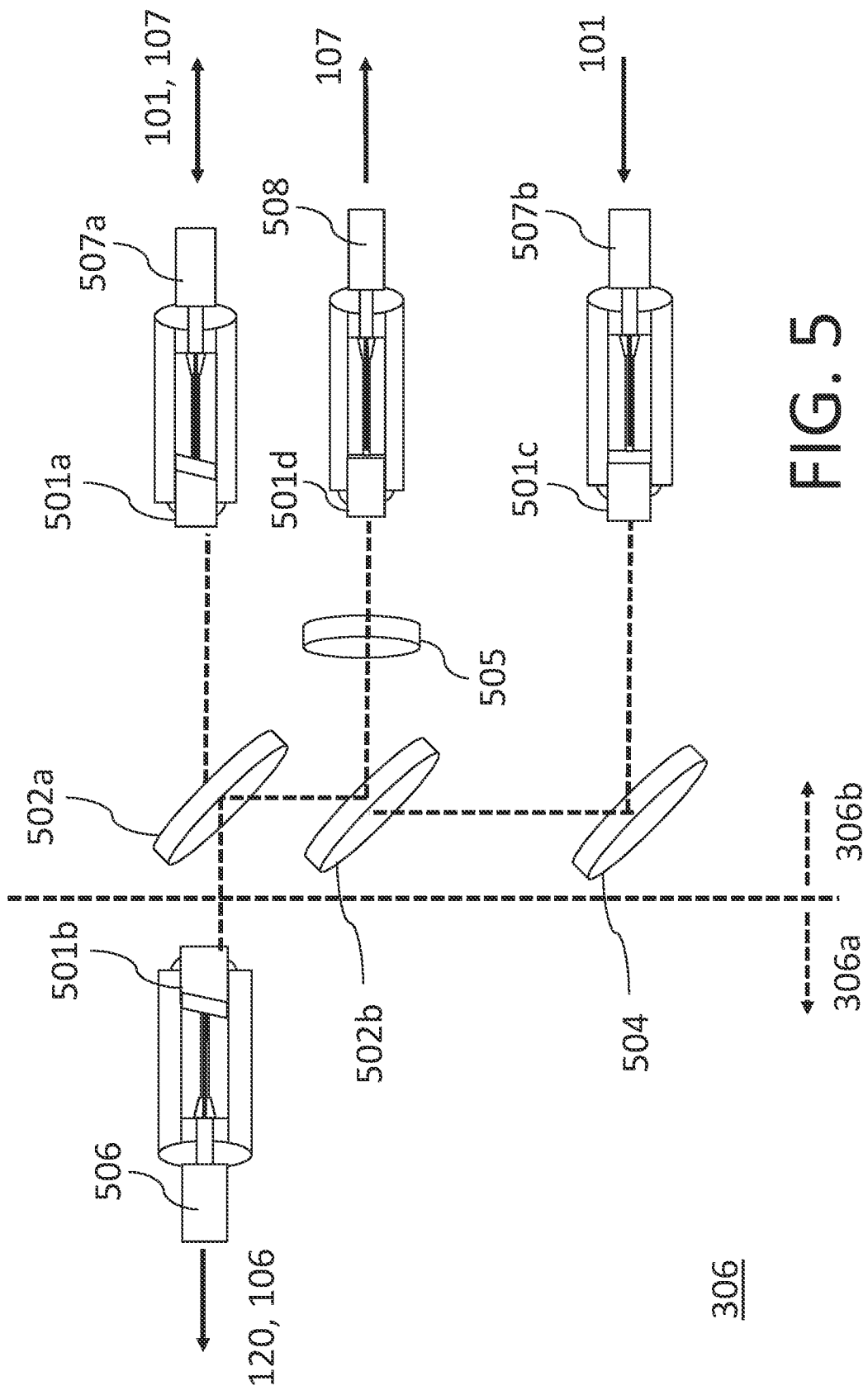
FIG. 5 is a diagram showing an embodiment of a fiber optic rotary joint that may be used with one or more detectors and/or PMTs in accordance with one or more aspects of the present disclosure.
Figure 6:
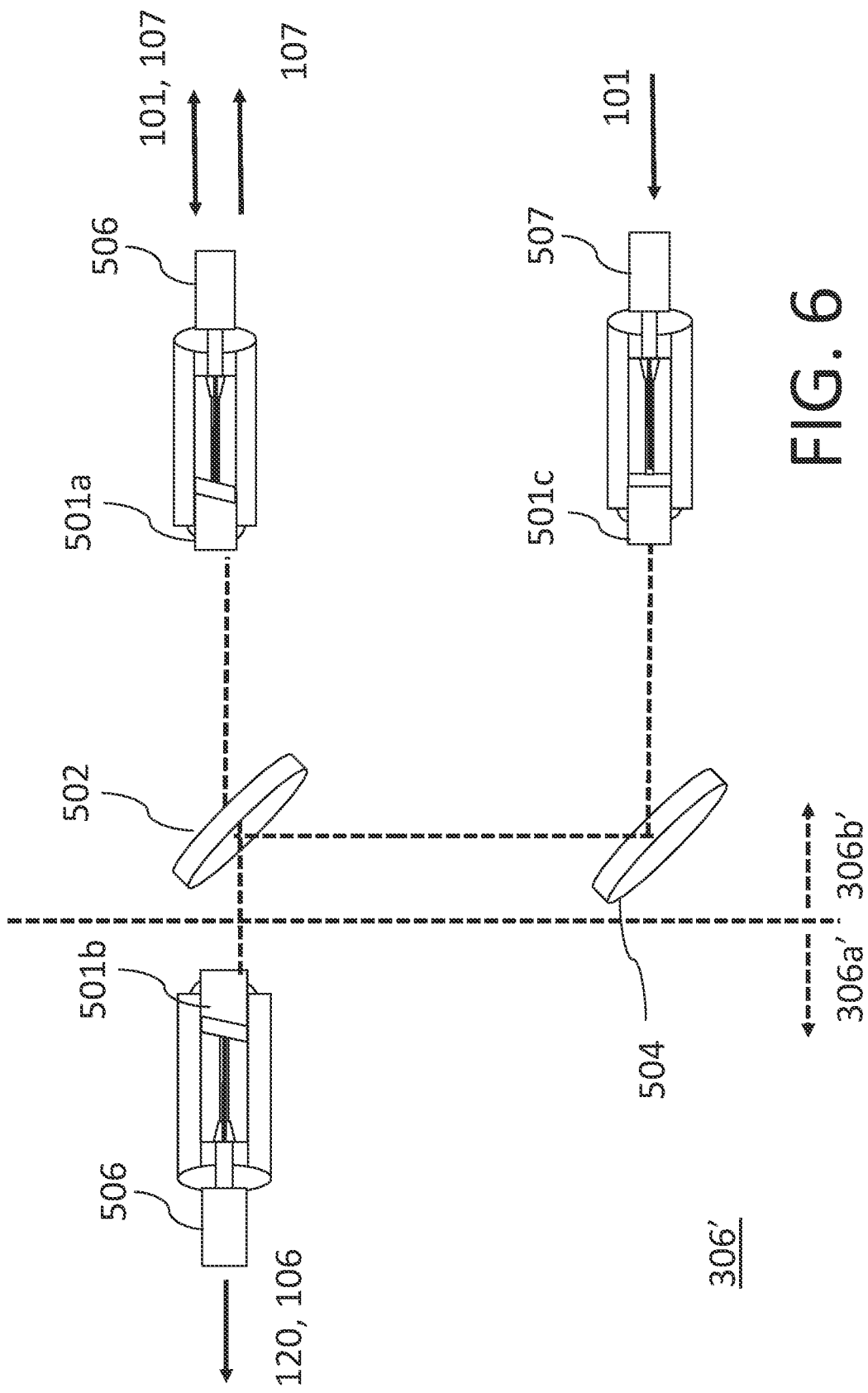
FIG. 6 is a diagram showing at least one embodiment of a free space beam combiner that may be used in at least one embodiment of a fiber optic rotary joint and that may be used with one or more detectors and/or PMTs in accordance with one or more aspects of the present disclosure.
Figure 8:
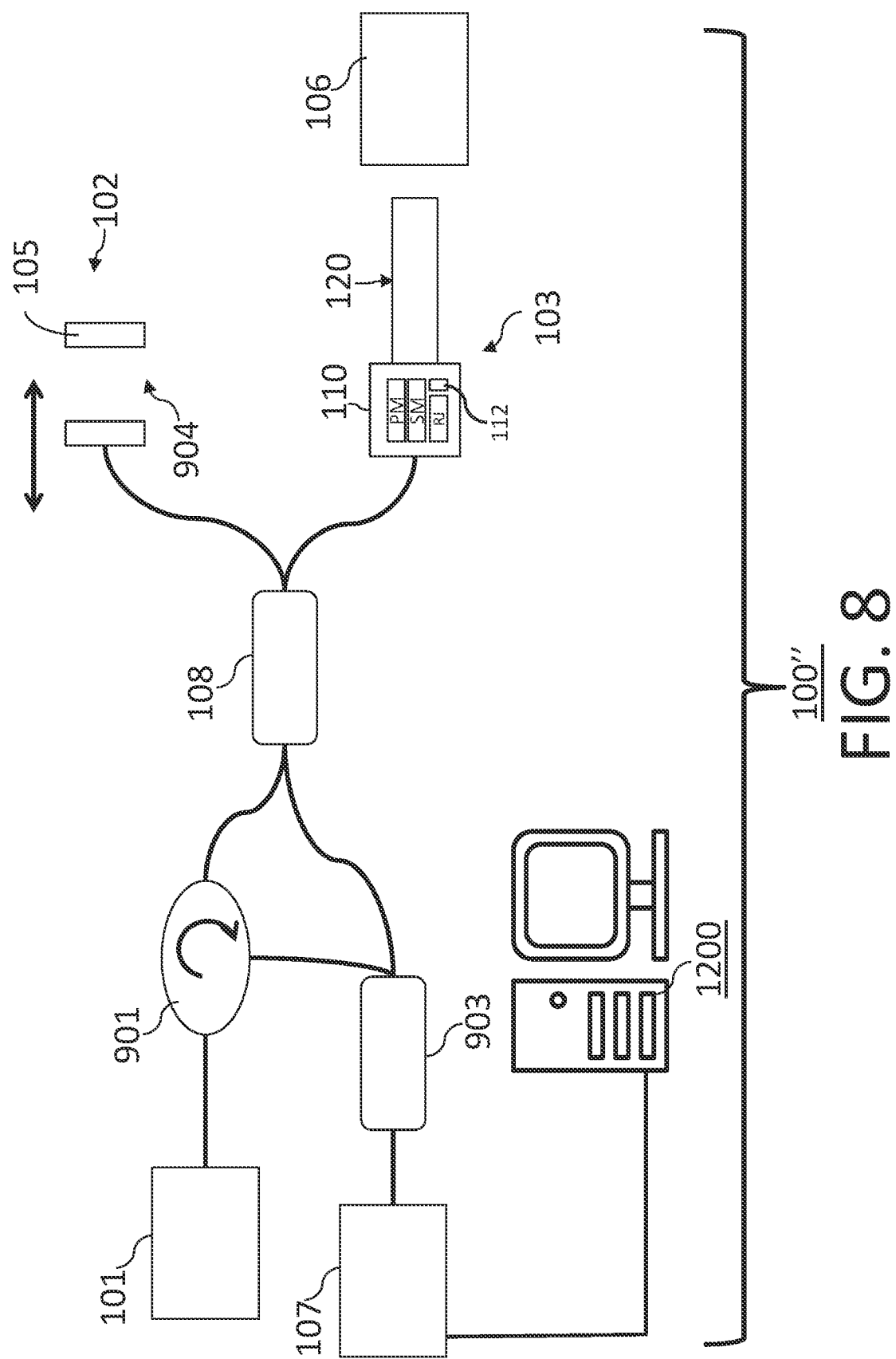
FIG. 8 is a diagram showing an embodiment of at least another system which can utilize one or more detectors/PMTs, and/or one or more measurement techniques, in accordance with one or more aspects of the present disclosure.
Figure 10:
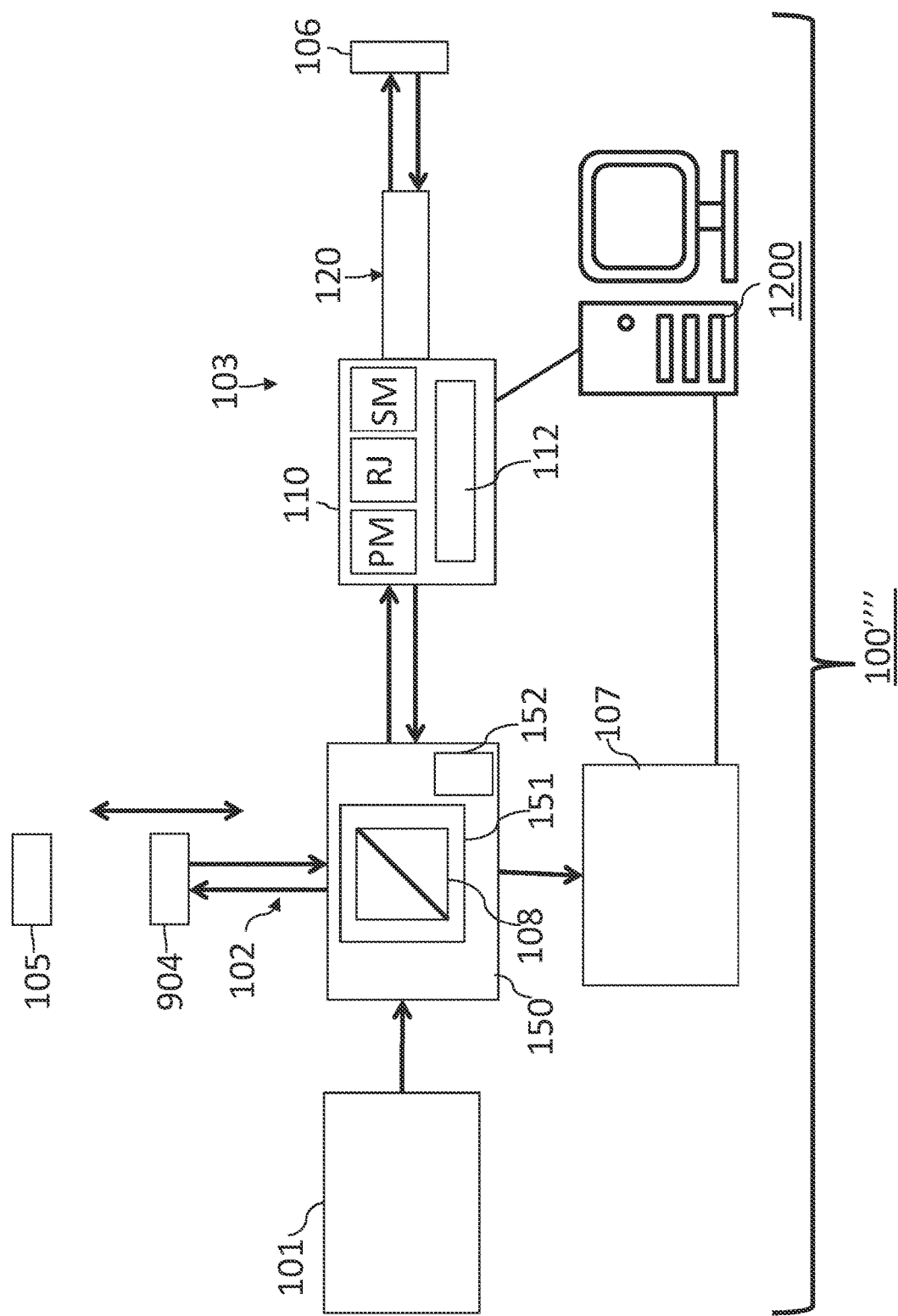
FIG. 10 is a diagram showing an embodiment of at least yet a further system which can utilize one or more one or more detectors/PMTs, and/or one or more measurement techniques, in accordance with one or more aspects of the present disclosure.

In one or more embodiments, the patient user interface 110 may comprise or include a connection component (or interface module), such as a rotary junction (e.g., the rotary junction 306 or 306' as shown schematically in FIGS. 2B and 5-6, the RJ of FIG. 8, the RJ of FIG. 10, another rotary junction discussed herein, etc.), to connect one or more components, such as one or more components of a probe (e.g., a catheter 120 (see e.g., FIGS. 1-4)), a needle, a capsule, a patient interface unit (e.g., the patient interface unit 110), etc., to one or more other components, such as, an optical component, a light source (e.g., the light source 101), a deflection section (e.g., such as the deflection or deflected section, which is a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc.), the sample arm 102, a motor that operates to power the connection component and/or the patient user interface 110, etc. For example, when the connection member or interface module is a rotary junction, preferably the rotary junction operates in the same or similar fashion as the rotary junction 306 and/or 306' discussed herein). In one or more other embodiments, the rotary junction may be at least one of: a contact rotary junction, a lenseless rotary junction, a lens-based rotary junction, or other rotary junction known to those skilled in the art.

In at least one embodiment, the PIU 110 may include a FORJ (such as the rotary joint 306 discussed herein, such as the rotary joint 306' discussed herein, such as the one or more embodiments of the RJ discussed herein, etc.), a rotational motor and translation motorized stage (see e.g., portion 139 of PIU 110 as shown in FIG. 2B), and a catheter connector (see e.g., portion 141 of the PIU 110 as shown in FIG. 2B). The PIU 110 may further include a free space beam combiner along with the FORJ, rotational motor and translation motorized stage, and/or catheter connector. The FORJ allows uninterrupted transmission of an optical signal while rotating the double clad fiber (e.g., the DCF 506) along the fiber axis. The FORJ may have a free space optical beam combiner consisting of a rotor and stator (see e.g., rotor 306a, 306a' and stator 306b, 306b' as shown in FIGS. 5-6 and as discussed further below), and the FORJ may have a free space optical beam coupler that operates to separate a rotor and a stator (see e.g., rotor 306a, 306a' and stator 306b, 306b' as shown in FIGS. 5-6 and as discussed further below).

FIG. 5 shows a configuration of a free space beam combiner and FORJ in accordance with at least one embodiment of the present disclosure. In an OCT and fluorescence system (such as the system 100a of FIG. 2A and/or the system 100' as shown in FIG. 2B), the stator (e.g., the stator 306b of FIG. 5) comprises at least two (2) optical fibers for OCT and excitation (see e.g., single mode fiber 507a of FIG. 5 that operates for OCT light source delivery and light detection; single mode fiber 507b of FIG. 5 that operates to work with the excitation light source 107 (e.g., light source 101 of the fluorescence sub-system or portion of system 100a of FIG. 2A and/or of system 100' of FIG. 2B); etc.). Each fiber has a lens at the beam combiner side of each fiber (e.g., the single mode fiber 507a is connected to a GRIN lens 501a as shown in FIG. 5; the multi-mode fiber 508 is connected to a GRIN lens 501d as shown in FIG. 5; the single mode fiber 507b is connected to a GRIN lens 501c as shown in FIG. 5; etc.). The rotor (e.g., the rotor 306a of FIG. 5) may be made of a double clad fiber (e.g., the double clad fiber 506) with a fiber connection at the catheter (e.g., the catheter 120) side and a lens (e.g., a GRIN lens 501b as shown in FIG. 5) at the beam combiner side. Then, the fiber connector of the rotor (e.g., the rotor 306a) is connected to the optical probe (e.g., the optical probe 124 via the catheter 120 as shown in FIGS. 4-5), and the stator (e.g., the stator 306b) is connected to the optical sub-systems (as shown schematically in FIGS. 5-6). For example, in at least one embodiment as best seen schematically in FIG. 5, the single mode fiber 507a is connected to the OCT light source (e.g., the light source 1i) and the detection elements (e.g., the at least one detector 107) of the OCT sub-system, the multi-mode fiber 508 is connected to the fluorescence detection elements (e.g., the at least one detector 107) of the fluorescence sub-system), and the single mode fiber 507b is connected to the excitation light source (e.g., the light source 1i) of the fluorescence sub-system. The rotational motor (e.g., the rotational motor 139) delivers the torque to the rotor (e.g., the rotor 306a). Also, the translation motorized stage is used for a pullback such that the beam is scanned inside the lumen sample in a helical manner. The catheter connector (e.g., the catheter connector 141 as shown schematically in FIG. 2B) is connected to the catheter (e.g., the catheter 120). In one or more embodiments, the rotor or rotor may include or may comprise a double clad fiber with a lens to make a collimated beam. The rotor may be connected to the optical probe, and the stator may be connected to the optical sub-systems. The rotational motor delivers the torque to the rotor. Also, the translation motorized stage may be used for a pullback as aforementioned.

In one or more embodiments, the free space beam combiner may have dichroic filters (e.g., the dichroic filter(s) 502a discussed herein) to separate different wavelength lights (OCT, excitation light, and Raman and auto-fluorescence lights in one or more embodiments). The beam combiner also may include or may comprise low-pass filters or band-pass filters in front of the Raman and auto-fluorescence channel to eliminate excitation light because of minimized excitation light noises at the fluorescence detector (e.g., the one or more detectors 107 of the fluorescence sub-system). The cut-off wavelength of the filter (low-pass or band-pass) may be selected around from 645 to 700 nm (but is not limited to this range in one or more embodiments).

As best seen in FIG. 5, OCT light is collimated with a GRIN lens 501a from single mode fiber 507a. The collimated OCT light couples into the core of the double clad fiber 506 (of rotor 306a) via a dichroic filter 502a and a GRIN lens 501b. Also, the back scattered OCT light from the sample (e.g., the sample 106) goes back to the rotor 306a (via the catheter 120). The light is collimated with the GRIN lens 501b and couples into the single mode fiber 507a. In one or more embodiments, the magnification may be approximately or about 1, or is 1, in order to couple fiber efficiently because OCT light is delivered with reversible paths (for example, from stator 306b to rotor 306a and from rotor 306a to stator 306b). In one or more embodiments, coupling efficiency may be improved or maximized when having the magnification be approximately or about 1, or be 1.

One or more embodiments of how to couple OCT and excitation channels into a single core of a double clad fiber in a rotary junction may be used with one or more embodiments of the present disclosure. For example, one or more embodiments of how to couple OCT and excitation channels into a single core of a double clad fiber in a rotary junction may be used as discussed in U.S. Pat. Pub. No. 2018/0348439, published on Dec. 6, 2018, the disclosure of which is incorporated by reference herein in its entirety. One or more features of a rotary joint, a rotary junction, a FORJ, etc. may be used as discussed in U.S. Pat. Pub. No. 2018/0348439, published on Dec. 6, 2018, the disclosure of which is incorporated by reference herein in its entirety.

In one or more embodiments, as best seen in FIG. 5, dichroic filter 502a may be used for separating OCT light from the rest of excitation and fluorescence light. Dichroic filter 502b may be used for a separation of the excitation and fluorescence light. The mirror 504 is used to reflect the excitation light. The long-pass filter 505 may be used to filter out back-reflection and/or stray light of excitation light.

In one or more alternative embodiments, a free space beam combiner, which is located inside an FORJ, may be provided as shown in FIG. 6. The embodiment of FIG. 6 is the same as the embodiment shown in FIG. 5, with the following exceptions: the stator 306b' of the rotary junction 306' in FIG. 6 includes two optical fibers (and not three) because the multi-mode fiber 508 and the GRIN lens 501d are removed, and the stator 306b' of the rotary junction 306' includes a double clad fiber 506 being used with GRIN lens 501a (instead of the single mode fiber 507a as shown in FIG. 5). OCT light goes through the core of the double clad fiber 506 in the stator 306', and is then collimated with the GRIN lens 501a. The collimated light is coupled into the core of the double clad fiber 506 in the rotor 306a'. Excitation light, with wavelength shorter than that of OCT light, is converged and focused with the GRIN lens 501c at the middle (or at a predetermined position) of the optical path to GRIN lens 501b. Then, the light is coupled into mostly the core of the double clad fiber 506 in the rotor 306a' of the rotary junction 306'. In one or more embodiments, fluorescence light from the sample (e.g., the sample 106) may be delivered through mostly the clad of the double clad fiber 506 in rotor 306a'. Then, the light may be coupled into the clad of the double clad fiber 506 in the stator 306b'. To separate OCT light and fluorescence light, a double clad fiber coupler may be used either inside the PIU 110 or in the imaging subsystem. Dichroic filter 502 of FIG. 6 is used to separate excitation light and the rest of fluorescence and OCT lights. The double clad fiber 506 of the stator 306b' is connected to a core/clad beam splitter to separate OCT and fluorescence light. As such, a simple and compact FORJ may be achieved with this configuration because of a lack of the free-space optical fluorescence channel. Also, it may be easier to fabricate the beam combiner because OCT and fluorescence lights may be coupled using a common double clad fiber (e.g., the fiber 506). In one or more embodiments, fibers other than a DCF may be used. The FORJ 306' may be used in place of the FORJ 306 as discussed above as shown schematically in FIG. 2B. In one or more embodiments, a mirror, a ferrule, a sleeve and/or epoxy as discussed in the present disclosure may be optional, and the fibers, lenses and a dichroic filter may be used without one or more of the mirror, the ferrule, the sleeve and/or the epoxy.

Descriptions of like-numbered elements present in the system 100' and/or the rotary junction 306' and already described above, such as for the system 100, the system 100a, the rotary junction 306, the system 100'', the system 100''', any other system discussed herein, etc., shall not be repeated, and are incorporated by reference herein in their entireties.

In at least one embodiment, the console 1200, 1200' operates to control motions of the motor and translation motorized stage (hereinafter referred to as "motor" or "motor and stage") 139, acquires intensity data from the at least one detector(s) 107, and displays the scanned image (e.g., on a monitor or screen such as a display, screen or monitor 1209 as shown in the console 1200 of FIG. 12 and/or the console 1200' of FIG. 13 as further discussed below). In one or more embodiments, the console 1200, 1200' operates to change a speed of the motor 139 and/or to stop the motor 139. The motor 139 may be a stepping or a DC servo motor to control the speed and increase position accuracy.

In one or more embodiments, the console or computer 1200, 1200' operates to control motions of the rotary junction 306, the rotary junction 306', the motor 139, the catheter 120 and/or one or more other above-described components of the system 100, the system 100a, and/or the system 100' (and/or any other system discussed herein). In at least one embodiment, the console or computer 1200, 1200' operates to acquire intensity data from the at least one detector 107 of the OCT sub-system and the fluorescence sub-system, and displays the image(s) (e.g., on a monitor or screen such as a display, screen or monitor 1209 as shown in the console 1200 of FIG. 12 and/or the console 1200' of FIG. 13 as further discussed below). The output of the one or more components of the system 100, the system 100a, and/or the system 100' is acquired with the at least one detector 107 of the OCT sub-system and with the at least one detector 107 of the fluorescence sub-system, e.g., such as, but not limited to, photodiodes, Photomultiplier tube(s) (PMTs), line scan camera(s), or multi-array camera(s). Electrical analog signals obtained from the output of the system 100, the system 100a, and/or the system 100' or one or more components thereof are converted to digital signals to be analyzed with a computer, such as, but not limited to, the computer 1200, 1200' (e.g., as shown in FIGS. 1-4 and 12-13). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light.

Figure 7:
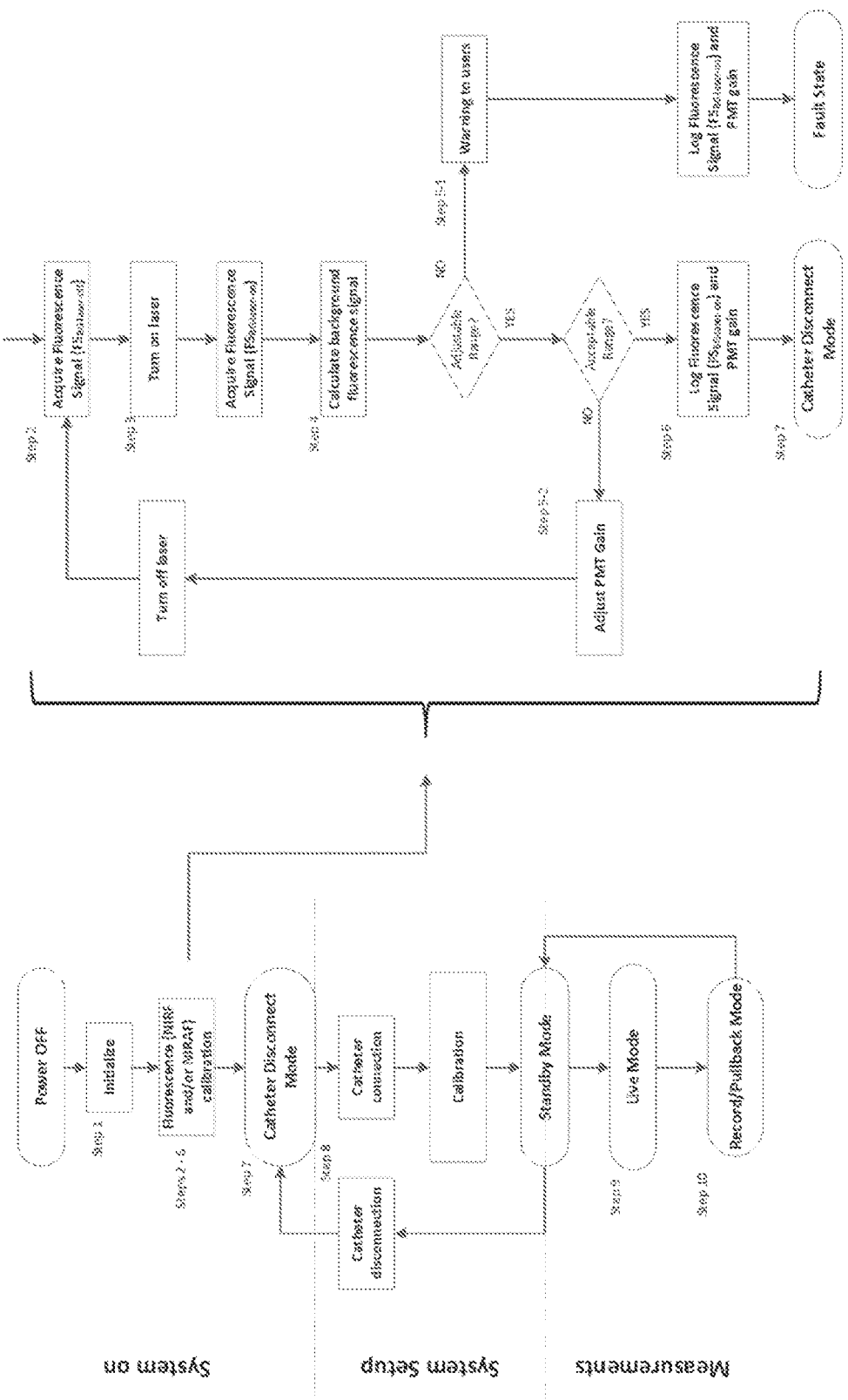
FIGS. 7A-7B show at least one embodiment of a measurement workflow or a method for performing measurement(s) for one or more apparatuses or systems in accordance with one or more aspects of the present disclosure.

In accordance with at least one aspect of the present disclosure and as aforementioned, one or more methods for measuring signals and/or performing fluorescence (NIRF and/or NIRAF) calibration are provided herein. FIGS. 7A-7B illustrate a flow chart of at least one embodiment of a method for performing measurements and/or performing fluorescence (NIRF and/or NIRAF) calibration. Preferably, the method(s) may include one or more of the following: (i) initializing a system (see e.g., step 1 of FIG. 7A); (ii) performing fluorescence (NIRF and/or NIRAF) calibration (see steps 2-6 of FIG. 7A and corresponding steps 2-6 of FIG. 7B as discussed further below); (iii) performing a catheter disconnect mode (see step 7 of FIG. 7A and corresponding step in FIG. 7B showing how this step is performed after fluorescence (NIRF and/or NIRAF) calibration is completed); (iv) performing catheter connection, calibration, and standby mode (if applicable) (see step 8 of FIG. 7A); (v) performing or entering Live Mode (see step 9 of FIG. 7A); and (vi) performing and/or entering a record and/or pullback mode (see step 10 of FIG. 7A). Preferably, the fluorescence (NIRF and/or NIRAF) calibration method(s) of FIG. 7B may include one or more of the following: (i) acquiring a fluorescence signal (e.g., $FS_{BG-laser-off}$) (see step 2 of FIG. 7B); (ii) turn on the laser or light source and acquire a fluorescence signal (e.g., $FS_{BG-laser-on}$) (see step 3 of FIG. 7B); (iii) calculate a background fluorescence signal, and determining whether the background fluorescence signal is in an adjustable range and/or in an acceptable range (see step 4 of FIG. 7B); (iv) in the event that the background fluorescence signal is not in an adjustable range and/or in an acceptable range, then the system gives the user(s) a warning and records the detector gain and/or PMT gain and the background fluorescence signal, and the system goes to a fault state (see "NO" in step 5-1 in FIG. 7B); or (v) in the event that the background fluorescence signal is in an adjustable range but is not in an acceptable range, then the system may adjust the fluorescence detector sensitivity to use the feedback circuits/algorithms to maintain the background fluorescence signal (For example, the PMT and/or detector may adjust the gain with the supplied control voltage. Then, turn off the laser and move to Step 2) (see "YES" in step 5-1 and "NO" in step 5-2 as shown in FIG. 7B); or (vi) in the event that the background fluorescence signal is in an adjustable range and is in an acceptable range, then the system may record the PMT gain and/or detector gain and the fluorescence signal (see step 6 in FIG. 7B), and return to step 7 of FIG. 7A to enter the catheter disconnect mode (see step 7 of FIG. 7B). One or more method embodiments may use the steps of FIG. 7A alone or in combination with the steps of FIG. 7B.

During the system on or system up portion (e.g., steps 1-7) of the method of FIG. 7A, application software may initialize and/or one or more processors may start to perform the method by performing the initialization step 1 of FIG. 7A. In one or more embodiments where initializing is occurring, calibrating PMT gain control may be performed by or to keep signals constant (e.g., without catheter or probe connections). In one or more embodiments, a system may have a lookup value to set in a factory, by a user, during manufacturing, etc., and such value(s) may be recorded or may record anode output (e.g., in a log).

During step 2 of FIG. 7A, a system (e.g., the system 100, the system 100a, the system 100', the system 100'', the system 100''', any other system discussed herein, etc.) may acquire the signals of the fluorescence detector (e.g., the detector(s) 107 of the fluorescence sub-system) while the excitation laser is off. The signals may be averaged (e.g., $FS_{BG\text{-}laser\text{-}off}$) to minimize the random noises.

During step 3 of FIG. 7A, the system (e.g., the system 100, the system 100a, the system 100', the system 100", the system 100''', any other system discussed herein, etc.) may turn on the excitation laser or light source, and then acquire the signals of the fluorescence detector (e.g., the detector(s) 107 of the fluorescence sub-system) while the excitation laser or light source (e.g., the light source 101) is on. The signals may be averaged (e.g., $FS_{BG\text{-}laser\text{-}on}$) to minimize the random noises.

During step 4 of FIG. 7A, the system (e.g., the system 100, the system 100a, the system 100', the system 100", the system 100''', any other system discussed herein, etc.) may calculate the system background fluorescence signal (e.g., $FS_{BG\text{-}laser\text{-}on} - FS_{BG\text{-}laser\text{-}off}$), and then may evaluate whether the signal is in an adjustable range (e.g., a predetermined range, a range set automatically by a system, a range set by a user, etc.) and/or in an acceptable range (e.g., a predetermined range, a range set automatically by a system, a range set by a user, etc.). In one or more embodiments, the adjustable range and the acceptable range may be similar or the same, or may be different (even if overlapping). This background fluorescence signal may come from the phosphor (e.g., the phosphor 140) in the PIU (e.g., the PIU 110). When the system powers up, this background fluorescence signal may be captured, so that the fluorescence detector sensitivity, such as, but not limited to, detector or PMT gain degradation, may be analyzed with the signal.

During step 5 of FIG. 7A and during step 5-1 of FIG. 7B, in case the background fluorescence signal is out of the adjustable range, the system indicates the aforementioned warning message(s) to user(s). Then, the system records the PMT gain and/or detector gain and the background fluorescence signal, and goes to a fault state.

During step 5 of FIG. 7A and during steps 5-1 to 5-2 of FIG. 7B, in a case where the background fluorescence signal is inside the adjustable range (see "YES" in step 5-1 of FIG. 7B) but is outside or is not in an acceptable range (see "NO" in step 5-2 of FIG. 7B), then the system may adjust the fluorescence detector sensitivity to use the feedback circuits/algorithms to maintain the background fluorescence signal (For example, the PMT and/or detector may adjust the gain with the supplied control voltage. Then, turn off the laser and move to Step 2). In the event that the background fluorescence signal is in the adjustable range (see "YES" in step 5-1 of FIG. 7B) and is in the acceptable range (see "YES" in step 5-2 of FIG. 7B), then the system may record the PMT gain and/or detector gain and the fluorescence signal (see step 6 in FIG. 7B), and return to step 7 of FIG. 7A to enter the catheter disconnect mode (see step 7 of FIG. 7B). One or more method embodiments may use the steps of FIG. 7A alone or in combination with the steps of FIG. 7B. In one or more embodiments, the default value for the adjustable range or the first set or predetermined range and/or the default value for the acceptable range or the second set or predetermined range may be derived from step 4 (by calculating the background fluorescence signal). The range limits for the adjustable range or the first set or predetermined range and/or the default value for the acceptable range or the second set or predetermined range may set automatically by the system or by a user manually (or may be adjusted manually by the user). For example, in one or more embodiments, if an acquired background signal is two times bigger or 0.5 times smaller, it may be out of the adjustable range such that the system goes to a fault condition or scenario. In one or more embodiments, if the background signal value is less than a first target value, then the background signal may be out of the adjustable range or the first set or predetermined range, and the background signal may be adjusted until it is within a set distance from the first target value (e.g., within +/−10% of the first target value, within +/−5% of the first target value, within +/−5-10% of the first target value, etc.). In one or more embodiments, if the background signal value is less than a second target value, then the background signal may be out of the acceptable range or the second set or predetermined range, and the background signal may be adjusted until it is within a set distance from the second target value (e.g., within +/−10% of the second target value, within +/−5% of the second target value, within +/−5-10% of the second target value, etc.). In one or more embodiments, a background fluorescence signal may be determined to be out of the adjustable range or first set or predetermined range and/or out of the acceptable range or second set or predetermined range in a case where the obtained background fluorescence signal is negative. In one or more embodiments, a system may set the first value and/or second target value based on values stored in a log file, values automatically set by the system, values previously used by the system, and/or values set by a user of the system. In one or more embodiments, when a system operates, every time a background fluorescence signal is saved, the system may check if there is a big change from the last or prior use of the background fluorescence signal to help determine whether the background fluorescence signal is in or out of the adjustable range or the first set or predetermined range and/or is in or out of the acceptable range or the second set or predetermined range.

During step 7 of FIGS. 7A and 7B, the system may be in a catheter disconnect or disconnected mode, and the system may be waiting for a catheter connection.

During the system setup process portion of the method(s) of FIG. 7A and in step 8, in a case where a catheter (e.g., the catheter 120) is connected to the system (e.g., mechanically and optically), the system operates to perform calibration(s) automatically and/or manually. The calibration may be z-offset calibration for OCT to adjust the reference arm, and/or may be catheter background subtraction for fluorescence images. In one or more embodiments, the system may enter a standby mode, and, in the event where the system detects a catheter disconnection, the system may enter the catheter disconnect mode and return to step 7 (as shown in FIG. 7A). In the event that the catheter stays connected to the system, then the system may proceed to step 9 of FIG. 7A.

In the measurement(s) portion of the method(s) of FIG. 7A and in step 9, a user may use the system to perform live-view imaging (e.g., to obtain a real-time image(s)) to decide whether to acquire images of one or more imaging modalities discussed herein (such as, but not limited to, OCT images, MMOCT images, image(s) of any other imaging modality discussed herein, etc.). In the event that it is decided to obtain the one or more images, the system may proceed to step 10 of FIG. 7A.

In step 10 of FIG. 7A, the system operates (automatically or manually by a user) to perform a pullback and to record OCT signals and fluorescence signals to obtain the measurement(s) and/or image(s).

In one or more embodiments, in a case where a system initiates before a catheter attaches or is attached, the detector sensitivity and/or the PMT sensitivity may be analyzed as to whether the signals are in a normal range (e.g., an adjustable range, an acceptable range, an adjustable range and an acceptable range, etc.), such that the system operates to determine whether correct or incorrect fluorescence measurements may be provided. The system may record correct measurements or, in the case where an incorrect fluorescence measurement may be provided, the system may provide warnings to users and/or calibrate the detector sensitivity and/or the PMT sensitivity to control the gain with a feedback loop.

A computer, such as the console or computer 1200, 1200', may perform any of the aforementioned steps (e.g., steps 1-10 of FIG. 7A; steps 2-7 of FIG. 7B; etc.), for any system, FORJ, and/or detector discussed herein, including, but not limited to, the system 100, the system 100*a*, the system 100', FORJ 306, FORJ 306', detector(s) 107, etc.

In one or more embodiments, a SEE probe and/or system may use a FORJ (e.g., the FORJ 306, the FORJ 306', etc.) with a connection member or interface module. For example, the connection member or interface module may include a rotary junction for either a SEE probe. In such a SEE system, the rotary junction may be at least one of: a contact rotary junction, a lenseless rotary junction, a lens-based rotary junction, a rotary junction as described herein, etc. The rotary junction may be a one channel rotary junction or a two channel rotary junction. By way of at least one example, in a SEE device one or more light sources may be used, and the light may be split into at least two (2) wavelength ranges for use with one or more embodiments of a FORJ of the present disclosure.

Unless otherwise discussed herein, like numerals indicate like elements. For example, while variations or differences exist between FORJs and/or the systems, such as, but not limited to, the FORJ 306, the FORJ 306', the system 100, the system 100*a*, the system 100', etc., one or more features thereof may be the same or similar to each other, such as, but not limited to, the light source 101 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100*a*, the system 100', etc., as discussed herein. Those skilled in the art will appreciate that alternative embodiments of the system 100, the system 100*a*, the system 100', FORJ 306, FORJ 306', the detector(s) 107, and/or one or more like-numbered elements of one of such systems, FORJs, or detectors, while having other variations as discussed herein, may operate in the same or similar fashion to the like-numbered elements of any of the other systems (or component(s) thereof) or FORJs (or component(s) thereof) discussed herein. Indeed, while certain differences exist between the system 100 and the system 100*a* and/or the system 100', and between FORJ 306 and FORJ 306', as discussed herein, there are similarities. Likewise, while the console or computer 1200 may be used in one or more systems (e.g., the system 100, the system 100*a*, the system 100', a system for manufacturing an FORJ (e.g., the FORJ 306, the FORJ 306', etc.), etc.) and/or to control an FORJ (e.g., the FORJ 306, the FORJ 306', etc.), one or more other consoles or computers, such as the console or computer 1200', may be used additionally or alternatively.

There are many ways to compute rotation, intensity, or any other measurement discussed herein, and/or to control and/or perform measurement(s) and/or methods of detector or PMT gain control, digital as well as analog. In at least one embodiment, a computer, such as the console or computer 1200, 1200', may be dedicated to control and/or monitor a FORJ and devices, systems, methods and/or storage mediums for use therewith described herein.

A computer, such as the console or computer 1200, 1200', may perform any of the steps, processes, and/or techniques discussed herein for any apparatus and/or system being manufactured or used, including, but not limited to, apparatus or system 100, apparatus or system 100*a*, apparatus or system 100', apparatus or system 100", apparatus or system 100''', any of the embodiments shown in FIGS. 1-6, 8-10, and 12-13, any other apparatus or system discussed herein, etc.

In accordance with one or more further aspects of the present disclosure, bench top systems may be utilized with the techniques, such as, but not limited to, the image synchronization techniques, disclosed herein. FIG. 8 shows an example of a system (e.g., the system 100") that can utilize the measurement and detector gain and/or PMT gain control techniques for a bench-top such as for ophthalmic applications. A light from a light source 101 delivers and splits into a reference arm 102 and a sample arm 103 with a deflecting (or deflection) section 108. A reference beam goes through a length adjustment section 904 (which is optional in one or more embodiments) and is reflected from a reference mirror (such as reference mirror or reference reflection 105 shown in FIG. 1) in the reference arm 102 while a sample beam is reflected or scattered from a sample, target or object 106 in the sample arm 103 (e.g., via the PIU 110 and the catheter 120). In one embodiment, both beams combine at the deflecting/deflection section 108 and generate interference patterns. In one or more embodiments, the beams go to the combiner 903, and the combiner 903 combines both beams via the circulator 901 and the deflecting section 108. The combined beams preferably are delivered to one or more detectors (such as the one or more detectors 107). The output of the beam splitter (see e.g., beam splitter 104 in FIG. 1), the deflecting section 108, and/or an interferometer is continuously acquired with one or more detectors, such as the one or more detectors 107. The electrical analog signals are converted to the digital signals to analyze them with a computer, such as, but not limited to, the computer 1200 (see FIG. 1; also shown in FIGS. 2A-2B, 8-10 and 12 discussed further below), the computer 1200' (see e.g., FIG. 13 discussed further below), etc. Indeed, the embodiment shown in FIG. 8 may be used with one or more fluorescence sub-system(s) and/or one or more FORJs discussed herein.

Figure 9:
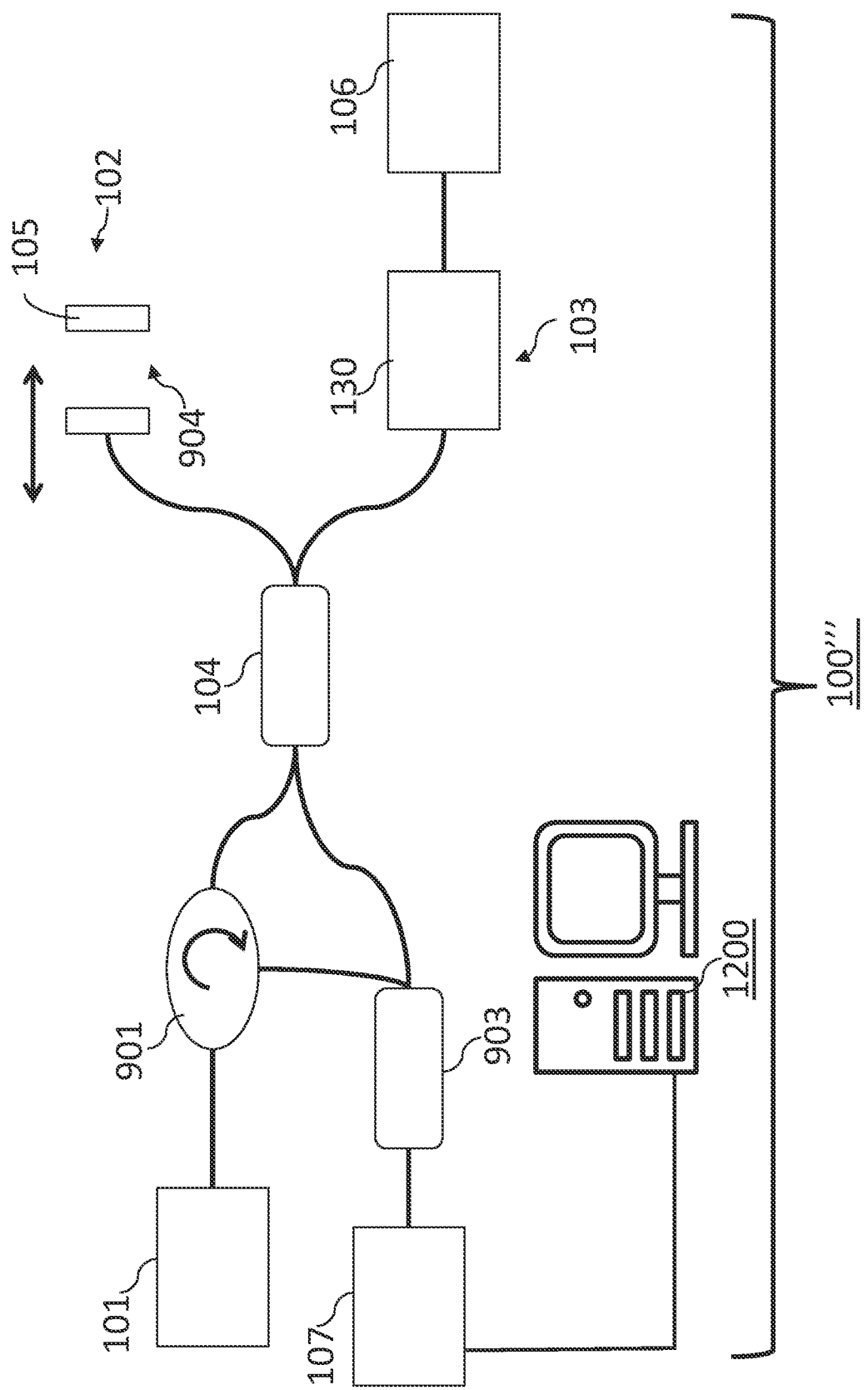
FIG. 9 is a diagram showing an embodiment of at least a further system which can utilize one or more one or more detectors/PMTs, and/or one or more measurement techniques, in accordance with one or more aspects of the present disclosure.

In one or more embodiments, the sample arm 103 may include a phase shift unit 130 for a bench top system(s) as shown in system 100''' in FIG. 9. The sample 106 may be located at the place of the mirror 105 used with the phase shift unit 130 (e.g., as shown in FIG. 1). A light from a light source 101 delivers and splits into a reference arm 102 and a sample arm 103 with a splitter 104. A reference beam goes through a length adjustment section 904 and is reflected from a reference mirror (such as reference mirror 105 shown in FIGS. 8-10) in the reference arm 102 while a sample beam is reflected or scattered from a sample, target and/or object 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the beam splitter 104 and/or an interferometer is continuously acquired with one or more detectors, such as the one or more detectors 107. The electrical analog signals are converted to the digital signals to analyze them with a computer. Indeed, the embodiment shown in FIG. 9 may be used with one or more fluorescence sub-system(s) and/or one or more FORJs discussed herein.

There are many ways to compute rotation, intensity, or any other measurement discussed herein, and/or to control and/or manufacture an MMOCT device/apparatus, system and/or storage medium, digital as well as analog. In at least one embodiment, a computer, such as the console or computer 1200, 1200', may be dedicated to control and/or use OCT and/or fluorescence (NIRF and/or NIRAF) devices, systems, methods and/or storage mediums for use therewith described herein. One or more other imaging modalities (e.g., NIRF, NIRAF, IVUS, etc.) may be used with one or more embodiments.

In accordance with one or more further aspects of the present disclosure, one or more other systems may be utilized with the image synchronization techniques disclosed herein. FIG. 10 shows an example of a system 100"" that may utilize the image synchronization techniques such as for ophthalmic applications. A light from a light source 101 delivers and splits into a reference arm 102 and a sample arm 103 with a deflecting section 108 (e.g., a beam splitter or other deflecting or deflected section discussed herein) located inside of an OCT imaging engine 150, which may also include an OCT interferometer 151 (which may house or include the deflecting section 108) and a swept source engine 152 in one or more embodiments. A reference beam may pass through a length adjustment section 904, which may operate to change the distance of a reference mirror (such as reference mirror or reference reflection 105; also shown in FIG. 1) and is reflected from the reference reflection 105 in the reference arm 102 while a sample beam is reflected or scattered from a sample, target or object 106 in the sample arm 103. In one embodiment, both beams combine at the deflecting section 108 and generate interference patterns. In one or more embodiments, the combined beams are delivered to one or more detectors. The output of the interferometer 151 is continuously acquired with one or more detectors, such as the one or more detectors 107. The electrical analog signals are converted to the digital signals to analyze them with a computer, such as, but not limited to, the computer 1200 (see e.g., FIG. 1; also shown in FIGS. 2A-2B, 8-10 and 12 discussed further below), the computer 1200' (see e.g., FIG. 13 discussed further below), etc. In one or more embodiments, the sample arm 103 includes the PIU 110 and the catheter 120 so that the sample beam is reflected or scattered from the sample, target or object 106 as discussed herein. In one or more embodiments, the PIU 110 may include one or more motors to control the pullback operation of the catheter 120 (or one or more components thereof) and/or to control the rotation or spin of the catheter 120 (or one or more components thereof). For example, the PIU 110 may include a pullback motor (PM) and a spin motor (SM), and/or may include a motion control unit 112 that operates to perform the pullback and/or rotation features using the pullback motor PM and/or the spin motor SM. Additionally or alternatively, a pullback motor (e.g., the pullback motor 270, 570) and/or a rotary motor (e.g., the rotary motor 260, 560) as discussed above may be used. As discussed herein, the PIU 110 may include a rotary junction (e.g., rotary junction RJ as shown in FIGS. 8 and 10). The rotary junction RJ may be connected to the spin motor SM so that the catheter 120 may obtain one or more views or images of the sample 106. The computer 1200 (or the computer 1200') may be used to control one or more of the pullback motor PM, the spin motor SM and/or the motion control unit 112. An OCT system may include one or more of the OCT engine 150, a computer (e.g., the computer 1200, the computer 1200', etc.), the PIU 110, the catheter 120, a monitor, etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc. Moreover, the embodiment shown in FIG. 10 may be used with one or more fluorescence sub-system(s) and/or one or more FORJs discussed herein.

Unless otherwise discussed herein, like numerals indicate like elements. For example, while variations or differences exist between the systems/apparatuses, such as, but not limited to, the system 100, the system 100a, the system 100', the system 100", the system 100''', the system 100'''', the systems/apparatuses of FIGS. 1-10 and 12-13, etc. (e.g., differences between the position(s) of the reference reflection 105 (and/or reference arm 102) depending on the OCT and/or fluorescence system or method being used), one or more features thereof may be the same or similar to each other, such as, but not limited to, the light source 101, the deflecting section 108 or other component(s) thereof (e.g., the console 1200, the console 1200', etc.). Those skilled in the art will appreciate that the light source 101, the at least one detector 107 and/or one or more other elements of the system 100, may operate in the same or similar fashion to those like-numbered elements of one or more other systems, such as, but not limited to, the system 100a, the system 100', the system 100", the system 100''', the system 100'''', etc. as discussed herein. Those skilled in the art will appreciate that alternative embodiments of the system 100, the system 100a, the system 100', the system 100", the system 100''', the system 100'''', the systems/apparatuses of FIGS. 1-10 and 12-13, and/or one or more like-numbered elements of one of such systems, while having other variations as discussed herein, may operate in the same or similar fashion to the like-numbered elements of any of the other systems (or component(s) thereof) discussed herein. Indeed, while certain differences exist between the system 100, the system 100a, the system 100', the system 100", the system 100''', and the system 100'''', the systems/apparatuses of FIGS. 1-10 and 12-13, etc. as discussed herein, there are similarities between the apparatuses/systems discussed herein. Likewise, while the console or computer 1200 may be used in one or more systems (e.g., the system 100, the system 100a, the system 100', the system 100", the system 100''', the system 100'''', the systems/apparatuses of FIGS. 1-10 and 12-13, etc.), one or more other consoles or computers, such as the console or computer 1200', may be used additionally or alternatively.

In accordance with one or more aspects of the present disclosure, one or more methods for image synchronization are provided herein, and one or more methods for performing imaging are provided herein. FIG. 11 illustrates a flow chart of at least one embodiment of a method for performing imaging. Preferably, the method(s) may include one or more of the following: (i) splitting or dividing light into a first light and a second reference light (see step S4000 in FIG. 11); (ii) receiving reflected or scattered light of the first light after the first light travels along a sample arm and irradiates an object or a sample (see step S4001 in FIG. 11); (iii) receiving the second reference light after the second reference light travels along a reference arm and reflects off of a reference reflection (see step S4002 in FIG. 11); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 11). One or more methods may further include using low frequency monitors to update or control high frequency content to improve image quality. For example, one or more embodiments may use balanced detection, polarization diversity, automated polarization control, etc. and/or image synchronization to achieve improved image quality. In one or more embodiments, an imaging probe may be connected to one or more systems (e.g., the system 100, the system 100a, the system 100', the system 100", the system 100''', the system 100'''', the devices, apparatuses or systems of FIGS. 1-10 and 12-13, any other system or apparatus discussed herein, etc.) with a connection member or interface module. For example, when the connection member or interface module is a rotary junction for an imaging probe, the rotary junction may be at least one of: a contact rotary junction, a lensless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', etc. The detection fibers may surround the illumination fiber, and the detection fibers may or may not be covered by a grating, a spacer, a lens, an end of a probe or catheter, etc.

There are many ways to compute power and/or perform measurement(s) and/or control a detector gain and/or a PMT gain, digital as well as analog. In at least one embodiment, a computer, such as the console or computer 1200, 1200', may be dedicated to the control and the monitoring of the OCT and/or fluorescence devices, systems, methods and/or storage mediums described herein.

The electric signals used for imaging, taking measurement(s), and/or performing gain control may be sent to one or more processors, such as, but not limited to, a computer 1200 (see e.g., FIGS. 1-10 and 12), a computer 1200' (see e.g., FIG. 13), etc. as discussed further below, via cable(s) or wire(s), such as, but not limited to, the cable(s) or wire(s) 113 (see FIG. 13).

Figure 12:
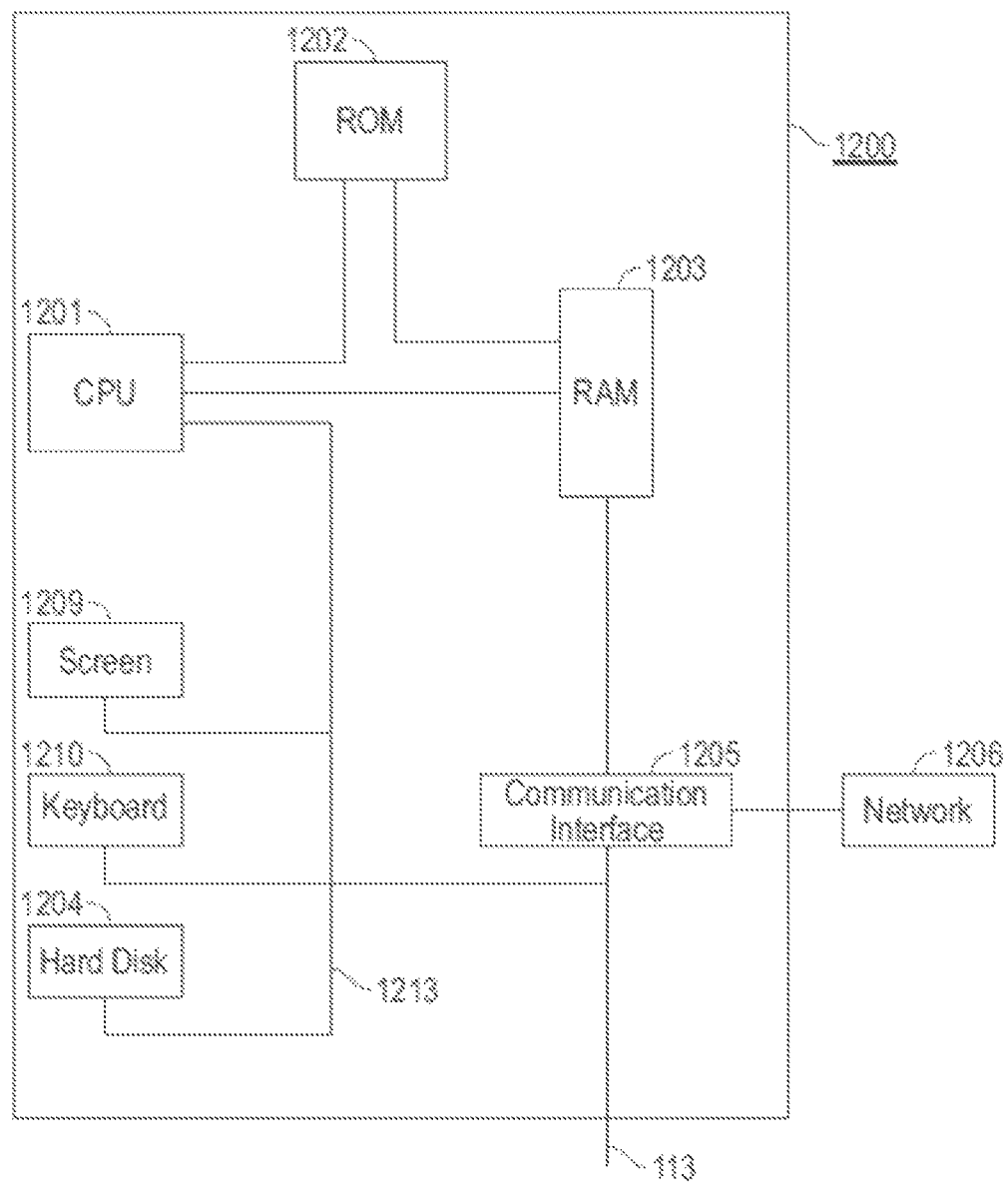
FIG. 12 shows a schematic diagram of an embodiment of a computer that may be used with one or more embodiments of at least one apparatus, system, method, and/or storage medium, including, but not limited to, for controlling one or more detectors/PMTs, and/or performing one or more measurement techniques, in accordance with one or more aspects of the present disclosure.

Various components of a computer system 1200 (see e.g., the console or computer 1200 as shown in FIGS. 1-6 and 8-10) are provided in FIG. 12. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 12). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a FORJ or a device or system using same, such as, but not limited to, the system 100, the system 100a, the system 100', the system 100", the system 100''', the system 100'''', etc. discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The computer system 1200 may include one or more additional processors in addition to CPU 1201, and such processors, including the CPU 1201, may be used for controlling and/or manufacturing a FORJ, and/or a device, system or storage medium for use with same. The system 1200 may further include one or more processors connected via a network connection (e.g., via network 1206). The CPU 1201 and any additional processor being used by the system 1200 may be located in the same telecom network or in different telecom networks (e.g., performing, manufacturing, controlling and/or using technique(s) may be controlled remotely).

Figure 13:
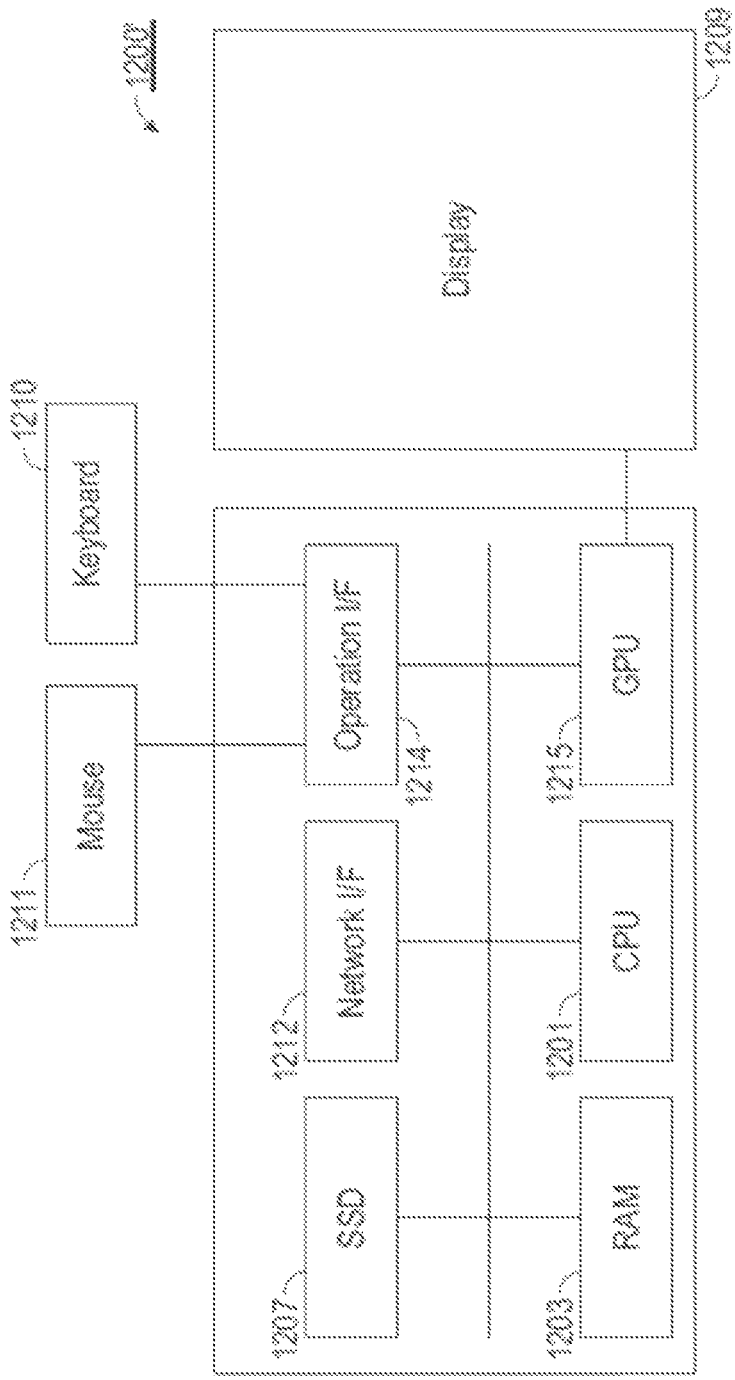
FIG. 13 shows a schematic diagram of another embodiment of a computer that may be used with one or more embodiments of at least one apparatus, system, method, and/or storage medium, including, but not limited to, for controlling one or more detectors/PMTs, and/or performing one or more measurement techniques, in accordance with one or more aspects of the present disclosure.

The I/O or communication interface 1205 provides communication interfaces to input and output devices, which may include the light source 101, a FORJ (e.g., the FORJ 306, the FORJ 306', the RJ, etc.), a PM, a SM, unit 150, unit 112, a microphone, a communication cable and a network (either wired or wireless), a keyboard 1210, a mouse (see e.g., the mouse 1211 as shown in FIG. 13), a touch screen or screen 1209, a light pen and so on. The Monitor interface or screen 1209 provides communication interfaces thereto.

Any methods and/or data of the present disclosure, such as the methods for using a FORJ, and/or an OCT and/or fluorescence device, system or storage medium for use with same, for performing measurement(s), and/or for controlling detector gain or PMT gain as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 13), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, the processor of computer 1200', etc., as described above may be achieved utilizing suitable hardware, such as that illustrated in the figures. Functionality of one or more aspects of the present disclosure may be achieved utilizing suitable hardware, such as that illustrated in FIG. 12. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 12 or FIG. 13) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 13. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with a rotary junction (e.g., the FORJ 306, the FORJ 306', RJ of FIG. 8, RJ of FIG. 10, etc.), the motor 139, the motor PM, the motor SM, and/or one or more other components of a system (e.g., the system 100, the system 100a, the system 100', the system 100", the system 100''', the system 100'''', any other system discussed herein, etc.) via the operation interface 1214 or the network interface 1212. A computer, such as the computer 1200', may include the FORJ 306 or 306', the RJ, the PM, the SM, and/or the motor 139 in one or more embodiments. The operation interface 1214 is connected with an operation unit such as a mouse device 1211, a keyboard 1210 or a touch panel device. The computer 1200' may include two or more of each component. Alternatively, the CPU 1201 or the GPU 1215 may be replaced by the field-programmable gate array (FPGA), the application-specific integrated circuit (ASIC) or other processing unit depending on the design of a computer, such as the computer 1200, the computer 1200', etc.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the PUI 110, the rotary junction (e.g., the rotary junction 306, the rotary junction 306', the RJ, etc.), the motor 139, the motor PM, the motor SM, the catheter 120 and/or one or more other components of a system, such as the system 100, 100', 100a, 100", 100''', 100'''', etc., to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a system (e.g., the system 100, the system 100', the system 100a, the system 100", the system 100''', the system 100'''', etc.), for example when performing OCT, fluorescence, or other imaging technique (s). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 100a, the system 100', the system 100", the system 100''', the system 100'''', etc.) to set or change the imaging condition, and to start or end the imaging. The laser source 101 of an OCT sub-system and/or the laser source 101 of a fluorescence sub-system as aforementioned may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; 9,557,154 and Patent Application Publication Nos. US2017/0035281; WO2015/116951; WO2015/116939; WO2017/024145; and US2018/0017778, each of which patents, patent publications and patent application(s) are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374, 2016/0228097, 2018/0045501 and 2018/0003481, each of which patents, patent publications and patent application(s) are incorporated by reference herein in their entireties. As aforementioned, any feature or aspect of the present disclosure may be used with systems, apparatuses, methods, storage mediums or other aspects or features as discussed in U.S. Pat. Pub. No. U.S. Pat. Pub. No. 2018/0348439, published on Dec. 6, 2018, the disclosure of which is incorporated by reference herein in its entirety.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An optical system comprising:
an interference optical system that operates to: (i) receive and divide light from a light source into a first light with which an object or sample is to be irradiated and which travels along a sample arm of the interference optical system and a second reference light, (ii) send the second reference light along a reference arm of the interference optical system for reflection off of a reference reflection of the interference optical system, and (iii) generate interference light by causing reflected or scattered light of the first light with which the object or sample has been irradiated and the reflected second reference light to combine or recombine, and to interfere, with each other, the interference light generating one or more interference patterns;
one or more detectors that operate to continuously acquire the interference light and/or the one or more interference patterns to measure the interference or the one or more interference patterns between the combined or recombined light to obtain data for one or more imaging modalities; and
one or more processors that operate to:
control a gain for the one or more detectors such that the optical system achieves reliable or consistent measurement(s) for the one or more imaging modalities and/or such that the optical system performs one or more calibrations for the one or more imaging modalities;
perform a fluorescence calibration using one or more fluorescence signals;
calculate a background fluorescence signal, determine whether the background fluorescence signal is in an adjustable range or a first set or predetermined range, and determine whether the background fluorescence signal is in an acceptable range or in a second set or predetermined range; and
in a case where the background fluorescence signal is in the adjustable range or in the set or predetermined first range and is in the acceptable range or in the set or predetermined second range, then the one or more processors record the gain of the one or more detectors and the fluorescence signal, and the one or more processors return the optical system to a standby mode and/or a catheter disconnect mode.

2. The optical system of claim 1, further comprising wherein the one or more processors operate to control the gain for the one or more detectors and/or operate to perform the one or more calibrations for the one or more imaging modalities by further operating to one or more of the following:
(i) initialize the optical system;
(ii) perform or detect the catheter disconnect mode, wherein a catheter is disconnected or determined to be disconnected from the optical system, or perform connection of a catheter, perform the one or more calibrations, and perform or enter the standby mode;
(iii) perform or enter a Live Mode, the Live Mode operating to perform live view imaging and/or to obtain a real time image or images of the one or more imaging modalities to determine whether to acquire one or more images of the one or more imaging modalities; and/or
(iv) perform and/or enter, automatically or manually, a record mode and/or a pullback mode, the record mode operating to record data, and the pullback mode operating to start or perform a pullback of a catheter of the optical system.

3. The optical system of claim 1, further comprising wherein the one or more processors further operate to one or more of the following:
(i) acquire one or more fluorescence signals, $FS_{BG\text{-}laser\text{-}off}$, as at least one of the one or more fluorescence signals, where $FS_{BG\text{-}laser\text{-}off}$ indicates that the at least one of the one or more fluorescence signals are acquired while the light source or a laser signal is off;
(ii) turn on the light source or a laser signal from the light source and acquire one or more fluorescence signals, $FS_{BG\text{-}laser\text{-}on}$, as at least one of the one or more fluorescence signals, where $FS_{BG\text{-}laser\text{-}on}$ indicates that the at least one of the one or more fluorescence signals are acquired while the light source or the laser signal is on;
(iii) in a case where the background fluorescence signal is not in the adjustable range or the set or predetermined first range and/or is not in the acceptable range or the set or predetermined second range, then the one or more processors cause a warning to be displayed on a display of the optical system and record the gain of the one or more detectors and the background fluorescence signal, and the optical system enters or goes to a fault state; and/or
(iv) in the event that the background fluorescence signal is in the adjustable range or in the set or predetermined first range but is not in the acceptable range or is not in the set or predetermined second range, then the one or more processors adjust a fluorescence detector sensitivity of the one or more detectors to use feedback circuits or algorithms to maintain the background fluorescence signal.

4. The optical system of claim 1, further comprising wherein one or more of the following:
(i) the one or more detectors include or comprise one or more of the following: photodiodes, Photomultiplier tube(s) (PMTs), line scan camera(s), and/or multi-array camera(s);
(ii) in a case where the one or more processors use feedback circuits or algorithms, the one or more processors operate to adjust the gain of the one or more detectors with a supplied control voltage, and operate to turn off the light source or the laser signal of the light source, and then start the fluorescence calibration; and/or (iii) the one or more imaging modalities includes one or more of the following: Optical Coherence Tomography (OCT), single modality OCT, multi-modality OCT, swept source OCT, optical frequency domain imaging (OFDI), intravascular ultrasound (IVUS), another lumen image(s) modality, near-infrared spectroscopy, near-infrared fluorescence (NIRF), near-infrared auto-fluorescence (NIRAF), and an intravascular imaging modality.

5. The optical system of claim 1, further comprising wherein one or more of the following:

(i) in a case where the one or more processors perform an initialization of the optical system and perform the fluorescence calibration, the one or more processors operate to: calibrate the gain or a control of the one or more detectors by keeping or to keep signals constant or calibrate the gain or the control of the one or more detectors by keeping or to keep signals constant, the optical system being without catheter or probe connection(s);

(ii) the one or more processors use a lookup value or values, and such value(s) are recorded or are used to record an output in a log or logs;

(iii) the one or more processors acquire the one or more fluorescence signals, $FS_{BG\text{-}laser\text{-}off}$, as at least one of the one or more fluorescence signals, where $FS_{BG\text{-}laser\text{-}off}$ indicates that the at least one of the one or more fluorescence signals are acquired while the light source or a laser signal of the light source is off; and/or (iv) the one or more processors further operate to average the one or more fluorescence signals, $FS_{BG\text{-}laser\text{-}off}$, to minimize or reduce one or more random noises, and/or the one or more processors further operate to average one or fluorescence signals, $FS_{BG\text{-}laser\text{-}on}$, to minimize or reduce one or more random noises, as at least one of the one or more fluorescence signals, where $FS_{BG\text{-}laser\text{-}on}$ indicates that the at least one of the one or more fluorescence signals are acquired while the light source or the laser signal is on.

6. The optical system of claim 1, further comprising wherein the one or more processors operate to calculate the background fluorescence signal as $FS_{BG\text{-}laser\text{-}on} - FS_{BG\text{-}laser\text{-}off}$ and then evaluate whether the background fluorescence signal is one of the following: (i) in the adjustable range or the first set or predetermined range and/or in the acceptable range or in the second set or predetermined range; (ii) not in the adjustable range or in the set or predetermined first range and/or not in the acceptable range or in the set or predetermined second range; (iii) in the adjustable range or in the set or predetermined first range but not in the acceptable range or not in the set or predetermined second range; or (iv) in the adjustable range or in the set or predetermined first range and in the acceptable range or in the set or predetermined second range.

7. The optical system of claim 6, wherein the one or more processors further operate to determine whether accurate or correct measurements are obtainable based on the evaluation of the background fluorescence signal being in the adjustable range or in the set or predetermined first range and in the acceptable range or in the set or predetermined second range or whether incorrect or inaccurate measurements are obtainable otherwise such that the one or more processors and/or the optical system provide one or more warnings and/or calibrate a sensitivity of the one or more detectors to control the gain with a feedback loop.

8. The optical system of claim 1, further comprising a phosphor that operates to produce or send the background fluorescence signal, wherein the one or more processors further operate to obtain the background fluorescence signal from the phosphor and/or further operate to use the obtained background fluorescence signal to analyze or evaluate a sensitivity and/or a gain degradation of a fluorescence detector of the one or more detectors.

9. The optical system of claim 8, further comprising wherein one or more of the following:

(i) the phosphor emits emissions having wavelengths longer than a light or excitation light from the light source in a case where the phosphor is excited by the light or excitation light from the light source;

(ii) the emissions of the phosphor are one or more of the following: Raman, fluorescence, and/or auto-fluorescence; and/or (iii) in a case where the emissions are Raman emissions, the Raman scattering lights do not decay over time so that the Raman scattering lights operate to be used for calibration of the one or more detectors.

10. The optical system of claim 1, further comprising wherein one or more of the following:

(i) the adjustable range or the set or predetermined first range is one or more of the following: a default range obtained by calculating the background fluorescence signal, a default range obtained from a log file, a range automatically set by the optical system, a range set or adjusted by a user of the optical system, two times a target value at one end of the adjustable range or the set or predetermined first range and 0.5 times or half the size of the target value at another end of the adjustable range or the set or predetermined first range, a range having a first target value at one end of the adjustable range or the set or predetermined first range and having a second target value at another end of the adjustable range or the set or predetermined first range, based on prior values or ranges used for the adjustable range or the set or predetermined first range, and/or a range with positive values;

(ii) the acceptable range or the set or predetermined second range is one or more of the following: a default range obtained by calculating the background fluorescence signal, a default range obtained from a log file, a range automatically set by the optical system, a range set or adjusted by a user of the optical system, two times a target value at one end of the acceptable range or the set or predetermined second range and 0.5 times or half the size of the target value at another end of the acceptable range or the set or predetermined second range, a range having a first target value at one end of the acceptable range or the set or predetermined second range and having a second target value at another end of the acceptable range or the set or predetermined second range, based on prior values or ranges used for the acceptable range or the set or predetermined second range, and/or a range with positive values;

(iii) the background fluorescence signal is in the adjustable range or the set or predetermined first range in a case where the background fluorescence signal is one or more of the following: within a set distance from a target value, within +/−10% of the target value, +/−5% of the target value, within +/−5-10% of the target value, a positive value, a value equaling or being between a first value at one end of the adjustable range or of the set or predetermined first range and a second value at another end of the adjustable range or of the set or predetermined first range, and/or about the same as one or more previously used background fluorescence signals determined to be in the adjustable range or the set or predetermined first range; and/or (iv) the background fluorescence signal is in the acceptable range or the set or predetermined second range in a case where the background fluorescence signal is one or more of the following: within a set distance from a target value, within +/−10% of the target value, +/−5% of the target value, within +/−5-10% of the target value, a positive value, a value equaling or being between a first value at one end of the acceptable range or of the set or predetermined second range and a second value at another end of the acceptable range or of the set or predetermined second range, and/or about the same as one or more previously used background fluorescence signals determined to be in the acceptable range or the set or predetermined second range.

11. The optical system of claim 1, wherein:
(i) in a case where the optical system is in the standby mode or the catheter disconnect mode, the optical system is waiting for, and/or the one or more processors operate to detect, a connection of a catheter to the optical system; and/or
(ii) in a case where the optical system and/or the one or more processors detect a catheter disconnection, the optical system enters the standby mode and/or the catheter disconnect mode.

12. The optical system of claim 1, wherein, in a case where a catheter is connected to the optical system, the optical system and/or the one or more processors of the optical system operate to perform the one or more calibrations automatically and/or manually, and the one or more calibrations comprise one or more of the following: (i) the fluorescence calibration, (ii) a z-offset calibration for Optical Coherence Tomography (OCT) to adjust the reference arm where the one or more imaging modalities includes OCT, and/or (iii) catheter background subtraction for fluorescence images where the one or more imaging modalities includes fluorescence, near-infrared fluorescence (NIRF), and/or near-infrared auto fluorescence (NIRAF).

13. The optical system of claim 1, further comprising a fiber optic rotary joint (FORJ) comprising:
a beam combiner;
a rotor that operates to rotate and that includes a common optical fiber connected to or part of the beam combiner; and
a stator that operates to be stationary in the fiber optic rotary joint and that includes at least two optical fibers, a first of the at least two optical fibers operating to guide at least the first light and being connected to or part of the beam combiner and a second of the at least two optical fibers operating to guide a third light and being connected to or part of the beam combiner, wherein the beam combiner operates to combine the first and third lights from the at least two optical fibers such that the combined light couples, or substantially couples, into a core of the common optical fiber.

14. The system of claim 13, wherein the combined light operates to irradiate the sample, and the FORJ includes at least one dichroic filter to separate the combined light into OCT light to be transmitted to the at least one detector and into fluorescent light to be transmitted to at least another detector.

15. The system of claim 14, further comprising one or more of:
(i) at least two light sources, a first of the at least two light sources operating to produce the first light, which is an OCT light, and a second of the at least two light sources operating to produce the third light, which is an excitation light; and/or
(ii) at least one of a motor and a processor that operates to rotate the rotor of the FORJ.

16. A method for controlling an optical system having an interference optical system that operates to generate interference light and one or more interference patterns, and one or more detectors that operate to continuously acquire the interference light and/or the one or more interference patterns to measure the interference or the one or more interference patterns to obtain data for one or more imaging modalities, the method comprising:
controlling a gain for the one or more detectors such that the optical system achieves reliable or consistent measurement(s) for the one or more imaging modalities and/or such that the optical system performs one or more calibrations for the one or more imaging modalities;
performing a fluorescence calibration using one or more fluorescence signals;
calculating a background fluorescence signal, determining whether the background fluorescence signal is in an adjustable range or a first set or predetermined range, and determining whether the background fluorescence signal is in an acceptable range or in a second set or predetermined range; and
in ta case where the background fluorescence signal is in the adjustable range or in the set or predetermined first range and is in the acceptable range or in the set or predetermined second range, then recording the gain of the one or more detectors and the fluorescence signal, and returning the optical system to a standby mode and/or a catheter disconnect mode.

17. The method of claim 16, further comprising one or more of the following:
(i) initializing the optical system;
(ii) performing or detecting the catheter disconnect mode, wherein a catheter is disconnected or determined to be disconnected from the optical system, or performing connection of a catheter, performing the one or more calibrations, and performing or entering the standby mode;
(iii) performing or entering a Live Mode, the Live Mode operating to perform live view imaging and/or to obtain a real time image or images of the one or more imaging modalities to determine whether to acquire one or more images of the one or more imaging modalities; and/or
(iv) performing and/or entering, automatically or manually, a record mode and/or a pullback mode, the record mode operating to record data, and the pullback mode operating to start or perform a pullback of a catheter of the optical system.

18. The method of claim 16, further comprising one or more of the following:
(i) acquiring one or more fluorescence signals, $FS_{BG\text{-}laser\text{-}off}$, as one of the one or more fluorescence signals, where $FS_{BG\text{-}laser\text{-}off}$ indicates that the one or more fluorescence signals are acquired while a light source or a laser signal is off;
(ii) turning on a light source or a laser signal from the light source and acquiring one or more fluorescence signals, $FS_{BG\text{-}laser\text{-}on}$, as one of the one or more fluorescence signals, where $FS_{BG\text{-}laser\text{-}on}$ indicates that the one or more fluorescence signals are acquired while the light source or the laser signal is on;

(iii) in a case where the background fluorescence signal is not in the adjustable range or in the set or predetermined first range and/or is not in the acceptable range or in the set or predetermined second range, then displaying a warning on a display of the optical system and recording the gain of the one or more detectors and the background fluorescence signal, and having the optical system enter or go to a fault state; and/or (iv) in the event that the background fluorescence signal is in the adjustable range or in the set or predetermined first range but is not in the acceptable range or is not in the set or predetermined second range, then adjusting a fluorescence detector sensitivity of the one or more detectors to use feedback circuits or algorithms to maintain the background fluorescence signal.

* * * * *